(12) United States Patent
Arimoto et al.

(10) Patent No.: US 10,080,366 B2
(45) Date of Patent: Sep. 25, 2018

(54) AGENT FOR INCREASING SUGAR CONTENT IN FRUIT

(71) Applicant: RIKEN, Wako-shi (JP)

(72) Inventors: Yutaka Arimoto, Wako (JP); Takayuki Kashima, Kusatsu (JP)

(73) Assignee: RIKEN, Wako-Shi, Saitama (JP)

( * ) Notice: Subject to any disclaimer, the term of this patent is extended or adjusted under 35 U.S.C. 154(b) by 0 days.

(21) Appl. No.: 14/387,112

(22) PCT Filed: Mar. 22, 2013

(86) PCT No.: PCT/JP2013/058406
§ 371 (c)(1),
(2) Date: Sep. 22, 2014

(87) PCT Pub. No.: WO2013/141381
PCT Pub. Date: Sep. 26, 2013

(65) Prior Publication Data
US 2015/0057156 A1    Feb. 26, 2015

(30) Foreign Application Priority Data

Mar. 22, 2012    (JP) ................................. 2012-065780

(51) Int. Cl.
| | | |
|---|---|---|
| *A01N 59/06* | (2006.01) |
| *A01N 37/02* | (2006.01) |
| *A01N 37/04* | (2006.01) |
| *A01N 37/36* | (2006.01) |
| *A01N 59/00* | (2006.01) |
| *A01N 59/04* | (2006.01) |
| *A01N 59/26* | (2006.01) |
| *A01N 47/06* | (2006.01) |
| *A01G 7/00* | (2006.01) |
| *C05F 11/00* | (2006.01) |
| *C05B 7/00* | (2006.01) |
| *C05B 13/06* | (2006.01) |
| *C05D 1/00* | (2006.01) |
| *A23B 7/157* | (2006.01) |
| *C12G 1/02* | (2006.01) |
| *A23L 19/00* | (2016.01) |
| *C12G 1/00* | (2006.01) |

(52) U.S. Cl.
CPC .............. *A01N 47/06* (2013.01); *A01G 7/00* (2013.01); *A01N 37/02* (2013.01); *A01N 37/04* (2013.01); *A01N 37/36* (2013.01); *A01N 59/00* (2013.01); *A01N 59/04* (2013.01); *A01N 59/06* (2013.01); *A01N 59/26* (2013.01); *A23B 7/157* (2013.01); *A23L 19/03* (2016.08); *C05B 7/00* (2013.01); *C05B 13/06* (2013.01); *C05D 1/00* (2013.01); *C05F 11/00* (2013.01); *C12G 1/02* (2013.01); *A23V 2002/00* (2013.01); *C12G 1/00* (2013.01)

(58) Field of Classification Search
None
See application file for complete search history.

(56) References Cited

U.S. PATENT DOCUMENTS

| | | | |
|---|---|---|---|
| 8,404,619 B2* | 3/2013 | Kubota | ................. A01N 59/06 |
| | | | 504/125 |
| 2002/0137632 A1 | 9/2002 | Kawai | |
| 2008/0153703 A1 | 6/2008 | Kubota et al. | |

FOREIGN PATENT DOCUMENTS

| | | | |
|---|---|---|---|
| CN | 1781485 | * | 6/2006 |
| EP | 0934917 A3 | | 8/2000 |
| EP | 1854356 A1 | | 11/2007 |
| JP | 4-300808 A | | 10/1992 |
| JP | 6-080488 | | 3/1994 |
| JP | 6-172069 | | 6/1994 |
| JP | 11-292707 A | | 10/1999 |
| JP | 2001-010914 A | | 1/2001 |
| JP | 2001-190154 | | 7/2001 |
| JP | 2002-322008 A | | 11/2002 |
| JP | 2003-274761 A | | 9/2003 |
| JP | 2004-238248 | | 8/2004 |
| JP | 2006-193498 | | 7/2006 |
| JP | 2010-030998 A | | 2/2010 |
| JP | 2010-158207 A | | 7/2010 |
| JP | 2012-017293 A | | 1/2012 |
| SU | 719995 | * | 3/1980 |
| WO | WO 2006/090666 A1 | | 8/2006 |
| WO | WO 2007083445 | | 7/2007 |

OTHER PUBLICATIONS

Wenneker et al.( Use of potassium bicarbonate (Armicarb) on the control of powdery mildew (*Sphaerotheca mors-uvae*) of gooseberry (*Ribes uva-crispa*), Communications in Agricultural and Applied Biological Sciences (2010), 75(4), 563-568).*

Nigro et al.( Control of table grape storage rots by pre-harvest applications of salts, Postharvest Biology and Technology (2006), 42(2),142-9)).*

Conclusion on the peer review of the pesticide risk assessment of the active substance potassium hydrogen carbonate, EFSA Journal (2012), 10(1), 2524, 36 pp.*

Sawant et al.( Use of potassium bi-carbonates for the control of powdery mildew in table grapes, Acta Horticulturae (2008), 785(Proceedings of the International Symposium on Grape Production and Processing, 2006), 285-291).*

(Continued)

*Primary Examiner* — Alton N Pryor
(74) *Attorney, Agent, or Firm* — Buchanan, Ingersoll & Rooney PC

(57) ABSTRACT

Provided is a compound and composition capable of increasing a sugar content in a fruit by a simple method, without being restricted by a cultivation area of a plant or a climatic environment. The agent for increasing a sugar content in a fruit of a plant comprises a compound represented by the formula MX as an active ingredient, wherein M represents alkali metal ion or alkaline earth metal ion, and X represents carbonate ion, hydrogen carbonate ion, acetate ion, citrate ion, succinate ion, phosphate ion, hydrogen phosphate ion, or pyrophosphate ion.

8 Claims, 13 Drawing Sheets

(56) References Cited

OTHER PUBLICATIONS

Crisp et al.( An evaluation of biological and abiotic controls for grapevine powdery mildew. 2. Vineyard trials, Australian Journal of Grape and Wine Research (2006), vol. 12, No. 3, pp. 203-211, 23 refs.).*
Milling et al.( Armicarb®—a new bio-fungicide for use in organic and conventional fruit growing in Europe, Ecofruit. 15th International Conference on Organic Fruit-Growing. Proceedings for the conference, Hohenheim, Germany, Feb. 20-22, 2012 (2012), pp. 264-267, 5 refs.).*
Buchanan et al.( Control of *Drosophila* spp., *Carpophilus* spp. and *Ephestia figulilella* (Gregson) in sultana grapes grown for dried fruit, Australian Journal of Experimental Agriculture and Animal Husbandry (1984), vol. 24, No. 126, pp. 440-446, 2 fig., 5 refs.*
Baudoin et al.( Factors affecting photosynthesis after oil application to grapevine, Phytopathology (92, No. 6, Suppl., S142, 2002).*
Schilder et al.( Fungicide efficacy in controlling phomopsis in grapes, 2000, Fungic.Nematic.Tests (56, SMF23, 2001).*
Wilcox et al.( Evaluation of fungicide programs for control of grapevine powdery mildew, 1997, Fungic.Nematic.Tests (53, 107-08, 1998) 1 Tab).*
Shabi(Evaluations of strobilurin, dinocap and SBI fungicides, sulfur, potassium bicarbonate and oils for the control of grape powdery mildew (PM), 1995.).*
M.P. Serratosa et al.: "Sensory Analysis of Sweet Musts in Pedro Ximenez cv. Grapes Dried using Different Methods," S. Afr. J. Enology and Viticulture, vol. 33, No. 1, Jan. 1, 2012, pp. 14-20, XP055228383.
A. Slatnar et al.: "Influence of Sodium Bicarbonate, an Anti-Apple Scab Agent, on Quality Parameters of 'Golden Delicious' Apples," Europ. J. Hort. Sci., vol. 76, No. 3, Mar. 10, 2011, pp. 95-101, XP055228381.

J.M. Navarro et al.: "Changes in quality and yield of tomato fruit with ammonium, bicarbonate and calcium fertilisation under saline conditions," Journal of Horticultural Science & Biotechnology, vol. 80, No. 3, May 1, 2005, pp. 351-357, XP055228719.
J. Bialczyk et al.: "Fruit Yield of Tomato Cultivated on Media with Bicarbonate and Nitrate/Ammonium as the Nitrogen Source," Journal of Plant Nutrition, vol. 30, No. 1, Jan. 1, 2007, pp. 149-161, XP055228735.
M.D.C. Antunes et al.: "The Effect of Postharvest Treatments with Sodium Bicarbonate or Acetic Acid on Storage Ability and Quality of Fig Fruit," Acta Horticult., vol. 798, Jan. 1, 2008, pp. 279-284, XP009187192.
I. Reh et al.: "Control of Powder Mildew on Grapevine with Sodium Hydrogen Carbonate," Med. Fac. Landbouww. Univ. Gent, vol. 60, No. 2a, 1995, pp. 321-327, XP009187188.
A. Bybordi et al.: "Effects of the Foliar Application of Magnesium and Zinc on the Yield and Quality of Three Grape Cultivars Grown in the Calcareous Soils of Iran," Notulae Scientia Biologicae, Apr. 1, 2010, pp. 81-86, XP055228816.
Supplementary Search Report issued by the European Patent Office in corresponding European Patent Application No. 13765166.7 dated Dec. 3, 2015 (11 pages).
International Search Report (PCT/ISA/210) dated Jun. 25, 2013, by the Japanese Patent Office as the International Searching Authority for International Application No. PCT/JP2013/058406.
Written Opinion (PCT/ISA/237) dated Jun. 25, 2013, by the Japanese Patent Office as the International Searching Authority for International Application No. PCT/JP2013/058406.
Ismail et al., "Effects of Dipping Solutions on Air-Drying Rates of the Seedless Grapes", Food Science and Technology Research, Jul. 2008, pp. 547-552, vol. 14, No. 6.
Christensen et al., "The Raisin Drying Process", Harvesting and Drying Raisin Grapes, 2000 (month unknown), pp. 207-216.
Japanese Office Action dated Mar. 15, 2017, in corresponding Patent Application No. 2014-506304.

* cited by examiner

Influences of various salts on decrease in mass of fruit of grape (g/100g)

Influences of various salts on sugar content in fruit of grape (Sugar content at start of experiment and sugar content at the end (actually measured values))

FIG.9
(a)
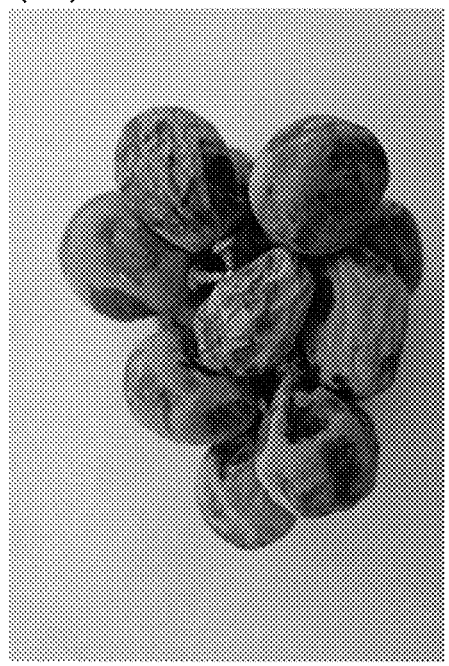
(b)
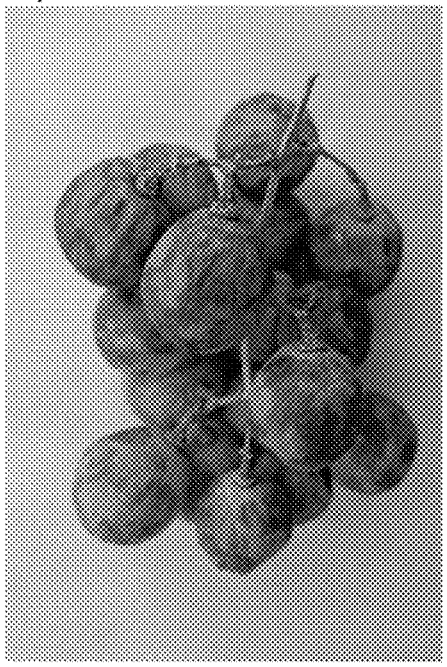
(c)
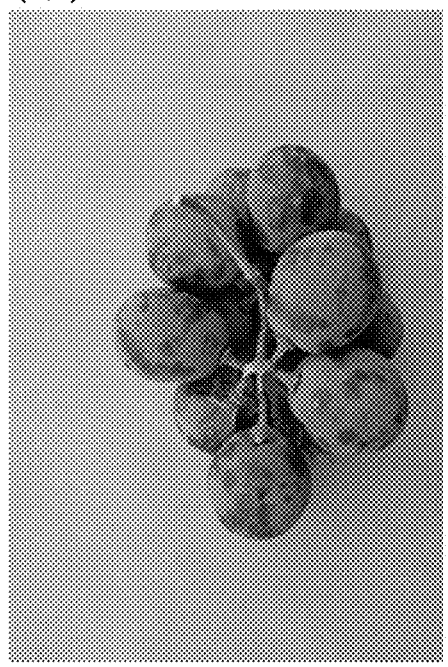

Influences of various salts on change in mass of fruit of grape

Influences of various salts on estimated amount of transpiration of water from fruit of grape Comparison between sugar content (actually measured value) in fruit on date of start of experiment and sugar content (calculated value) in fruit at the end of experiment

AGENT FOR INCREASING SUGAR CONTENT IN FRUIT

The entire disclosure of Japanese Patent Application No. 2012-065780 on the basis of which priority is claimed, including specification, claims, drawings and summary, is incorporated herein by reference in its entity. All publications, patents and patent applications cited herein are incorporated herein by reference in their entity.

TECHNICAL FIELD

The present invention relates to an agent for increasing a sugar content in a fruit of a plant and a method for increasing a sugar content in a fruit of a plant.

BACKGROUND ART

With the recent diversification of consumers' preferences, various types of alcoholic beverages have been produced. Among alcoholic beverages, wine is enjoyed by a wide range of generations, as well as beer, Japanese sake, and the like.

With the increased demand for wine, the areas where grape, which serves as a raw material of wine, is cultivated are extending from conventional warm areas to cool areas. As a result, the insufficient temperature during the cultivation period leads to an insufficient sugar content in the fruit, which necessitates chaptalization. However, there is such a problem that a wine chaptalized during its production is inferior in class to a non-chaptalized wine. For this reason, there are high demands for obtaining a wine which does not require the additional chaptalization during its production, and for obtaining a fruit of grape having a sugar content sufficient for a raw material of wine.

Noble rot wine and ice wine have been known as wines which are produced with the sugar content in the fruit of grape being increased.

Noble rot wine is a white wine made from a fruit of grape infected with a noble rot fungus called *Botrytis cinerea*. The noble rot fungus creates numerous holes on the skin of the fruit, and water in excess evaporates therethrough. Thus, the sugar content increases, which results in a very sweet wine with rich in aroma.

Regarding ice wine, the harvest time is delayed to winter, and the fruit of grape is frozen and thawed repeatedly several times in the climate. As a result, water in the fruit of grape gradually decreases, so that grape with a high sugar content is harvested. Hence, a sweet and aromatic wine can be produced.

Besides these methods, as a method for increasing a sugar content in a fruit using an agent, Patent Literature 1 describes a method in which a plant is grown, while a solution containing an iodine-cyclodextrin inclusion compound is sprayed to flowers or leaves of the plant.

CITATION LIST

Patent Literature

Patent Literature 1: Japanese Patent Application Publication No. 2002-322008

SUMMARY OF INVENTION

Technical Problems

However, the noble rot fungus, *Botrytis cinerea*, used to produce noble rot wine is a pathogenic fungus for various plants such as fruit plants, vegetables, and beans. In the case of grape, *Botrytis cinerea* acts as a pathogenic fungus, in general, and adheres to and rots grape during aging. For this reason, increasing the sugar content in the fruit without allowing grape to rot generates problems such as restrictions of the cultivation area and climatic environment.

Meanwhile, ice wine requires the repetition of freezing and thawing of the fruit of grape before the harvest, and hence has such a problem that ice wine cannot be produced in regions other than regions suitable for such freezing and thawing.

Accordingly, there is a high demand for a novel agent for increasing a sugar content in a fruit capable of increasing a sugar content in a fruit by a simple approach, irrespective of natural conditions.

The present invention has been made in view of the above-described problems, and is to provide a novel agent for increasing a sugar content in a fruit capable of increasing a sugar content in a fruit by a simple approach, without being restricted by a cultivation area or a climatic environment.

In addition, another object of the present invention is to provide a method for producing a dried grape by which the drying time can be made shorter than that in a conventional case.

Another object of the present invention is to provide an agent for preventing and/or treating a physiological plant disorder caused by calcium deficiency.

Another object of the present invention is to provide an agent for preventing fruit cracking of a fruit of a plant.

Another object of the present invention is to provide an amino acid concentration-increasing agent for increasing a concentration of an amino acid contained in a plant body.

Solution to Problems

The present inventors have conducted an intensive study to solve the above-described problems, and found that the use of a specific compound or a composition containing the compound remarkably increases the sugar content in a fruit of a plant.

Specifically, gist of the present invention is as follows.

1. An agent for increasing a sugar content in a fruit of a plant, comprising a compound represented by the formula MX as an active ingredient, wherein M represents alkali metal ion or alkaline earth metal ion, and X represents carbonate ion, hydrogen carbonate ion, acetate ion, citrate ion, succinate ion, phosphate ion, hydrogen phosphate ion, or pyrophosphate ion.
2. The agent for increasing a sugar content in a fruit according to the above-described 1, wherein M is alkali metal ion.
3. The agent for increasing a sugar content in a fruit according to the above-described 1 or 2, wherein M is sodium ion or potassium ion.
4. The agent for increasing a sugar content in a fruit according to any one of the above-described 1 to 3, wherein X is carbonate ion or hydrogen carbonate ion.
5. The agent for increasing a sugar content in a fruit according to any one of the above-described 1 to 4, further comprising a vegetable oil and/or fat.
6. The agent for increasing a sugar content in a fruit according to any one of the above-described 1 to 5, further comprising a surfactant.
7. A method for increasing a sugar content in a fruit of a plant, comprising applying to the plant the agent for increasing a sugar content in a fruit according to any one of the above-described 1 to 6.

8. The method according to the above-described 7, wherein the above-described agent for increasing a sugar content in a fruit is applied in a period from 2 months before an expected harvest date or a harvest date of the fruit to 2 months after the expected harvest date or the harvest date.
9. The method according to the above-described 7 or 8, wherein the compound represented by the formula MX is applied to the plant at a concentration in a range from 1 g/L to 100 g/L.
10. The method according to the above-described 7 or 8, wherein the compound represented by the formula MX is applied to the plant at a dose in a range from 1 kg/ha to 30 kg/ha.
11. A method for producing a fruit wine, comprising using as a raw material a fruit to which the agent for increasing a sugar content in a fruit according to any one of the above-described 1 to 6 has been applied.
12. A method for producing a dried grape, comprising adding a compound represented by the formula MX to a grape, wherein M represents alkali metal ion or alkaline earth metal ion, and X represents carbonate ion, hydrogen carbonate ion, acetate ion, citrate ion, succinate ion, phosphate ion, hydrogen phosphate ion, or pyrophosphate ion.
13. An agent for preventing and/or treating a physiological plant disorder caused by calcium deficiency, comprising a compound represented by the formula MX as an active ingredient, wherein M represents alkali metal ion or alkaline earth metal ion, and X represents carbonate ion, hydrogen carbonate ion, acetate ion, citrate ion, succinate ion, phosphate ion, hydrogen phosphate ion, or pyrophosphate ion.
14. An agent for preventing fruit cracking of a fruit of a plant, comprising a compound represented by the formula MX as an active ingredient, wherein M represents alkali metal ion or alkaline earth metal ion, and X represents carbonate ion, hydrogen carbonate ion, acetate ion, citrate ion, succinate ion, phosphate ion, hydrogen phosphate ion, or pyrophosphate ion.
15. An agent for increasing a concentration of an amino acid contained in a plant body, comprising a compound represented by the formula MX as an active ingredient, wherein M represents alkali metal ion or alkaline earth metal ion, and X represents carbonate ion, hydrogen carbonate ion, acetate ion, citrate ion, succinate ion, phosphate ion, hydrogen phosphate ion, or pyrophosphate ion.

Advantageous Effects of Invention

The present invention makes it possible to increase a sugar content in a fruit by a simple method, without being restricted by a cultivation area of a plant or a climatic environment.

The present invention also makes it possible to produce dried grape in a shorter drying time than in a conventional case.

The present invention makes it possible to prevent and/or treat a physiological plant disorder caused by calcium deficiency.

The present invention makes it possible to prevent fruit cracking of a fruit of a plant.

The present invention makes it possible to increase a concentration of an amino acid contained in a plant body.

BRIEF DESCRIPTION OF DRAWINGS

FIG. 9 shows photographs of the appearance of fruit of grape 20 days after application (March 30) in Example 5. Part (a) shows fruit of grape treated with potassium hydrogen carbonate (10 g/L), Part (b) shows fruit of grape treated with potassium hydrogen carbonate (5 g/L), and Part (c) shows untreated fruit of grape.

DESCRIPTION OF EMBODIMENTS

Figure 1:
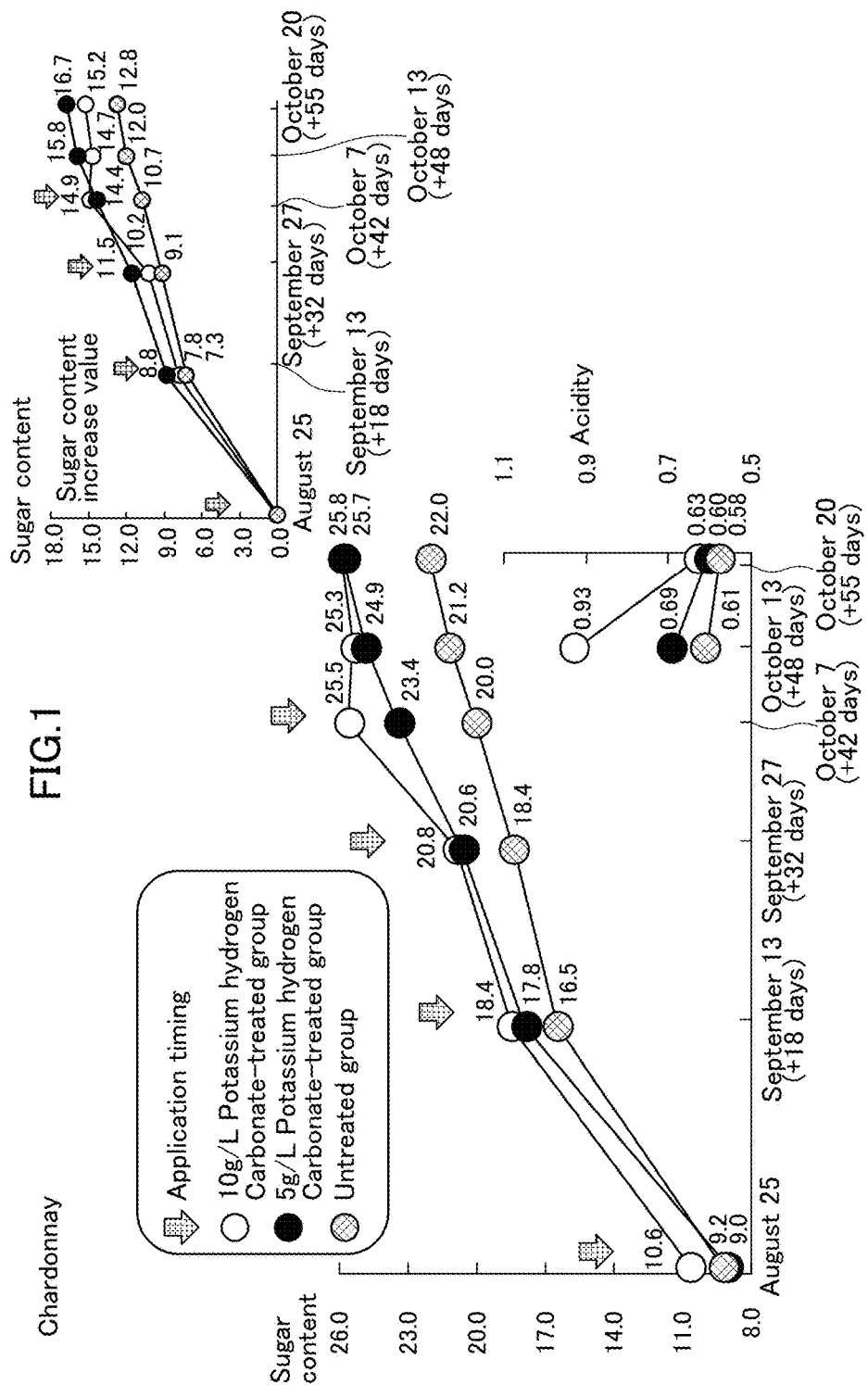
FIG. 1 is a graph showing changes in sugar content and acidity in a case where agents for increasing a sugar content in a fruit of the present invention were applied to Chardonnay in Example 1.
Figure 2:
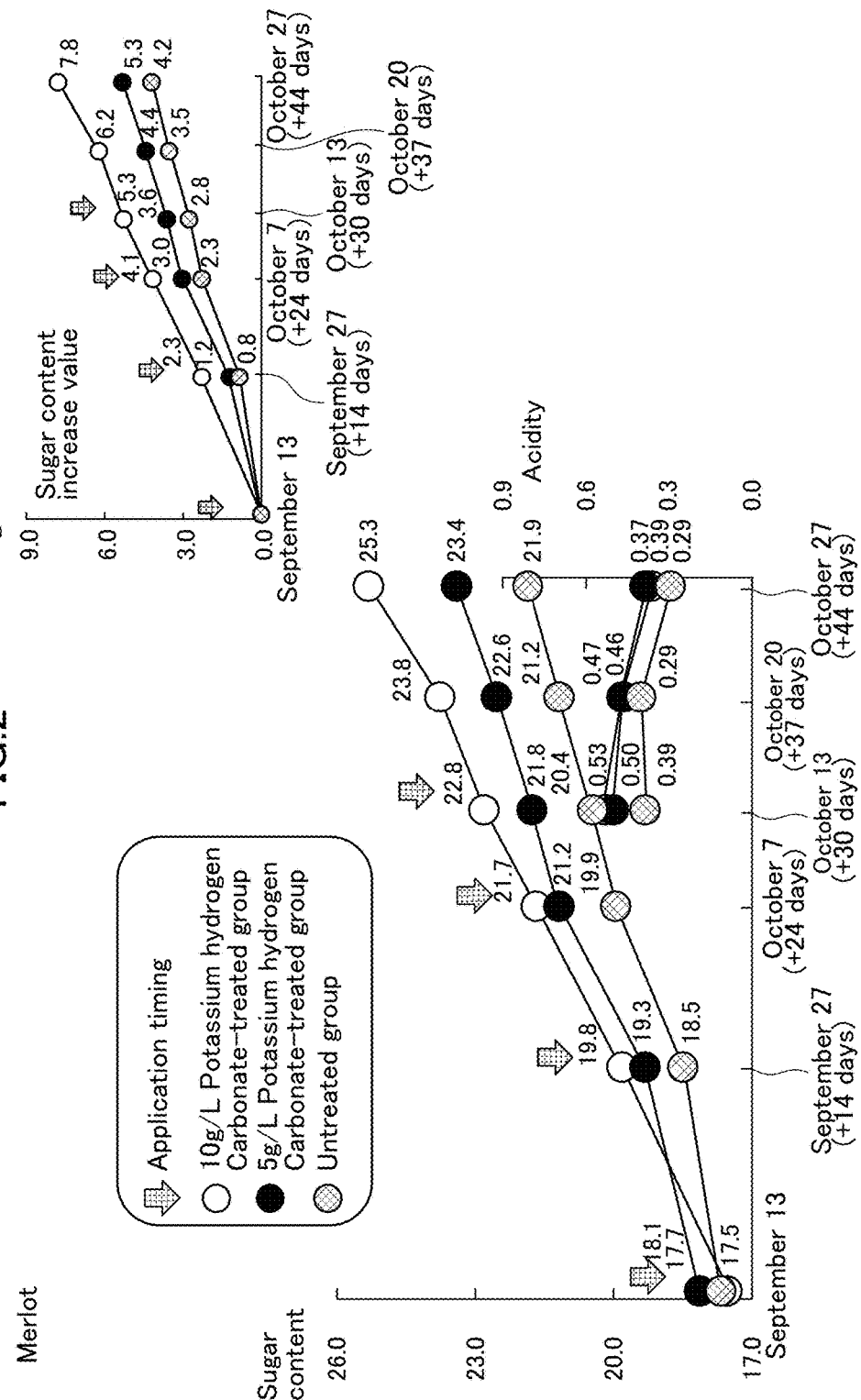
FIG. 2 is a graph showing changes in sugar content and acidity in a case where the agents for increasing a sugar content in a fruit of the present invention were applied to Merlot in Example 1.
Figure 3:
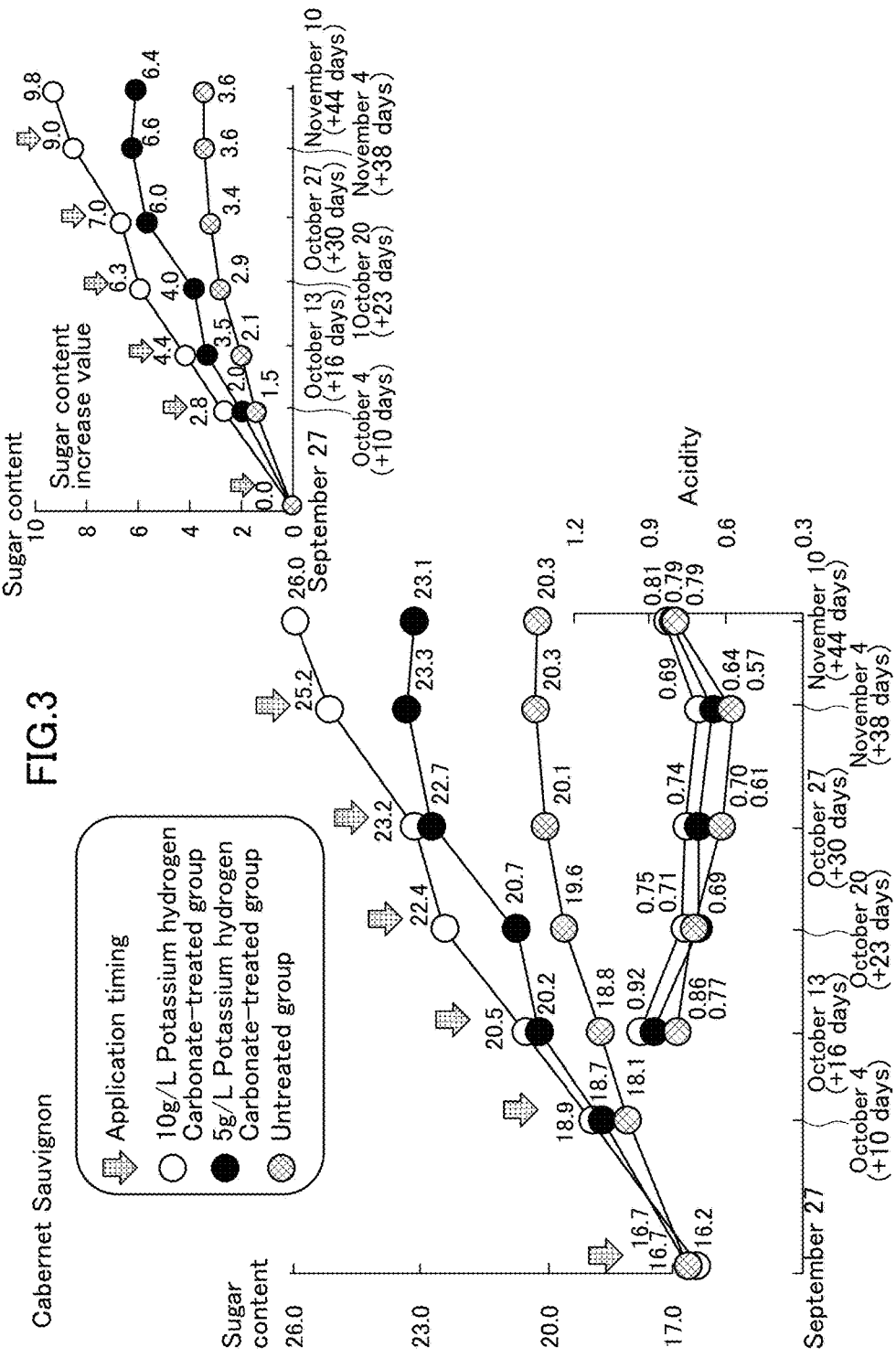
FIG. 3 is a graph showing changes in sugar content and acidity in a case where the agents for increasing a sugar content in a fruit of the present invention were applied to Cabernet Sauvignon in Example 1.
Figure 4:
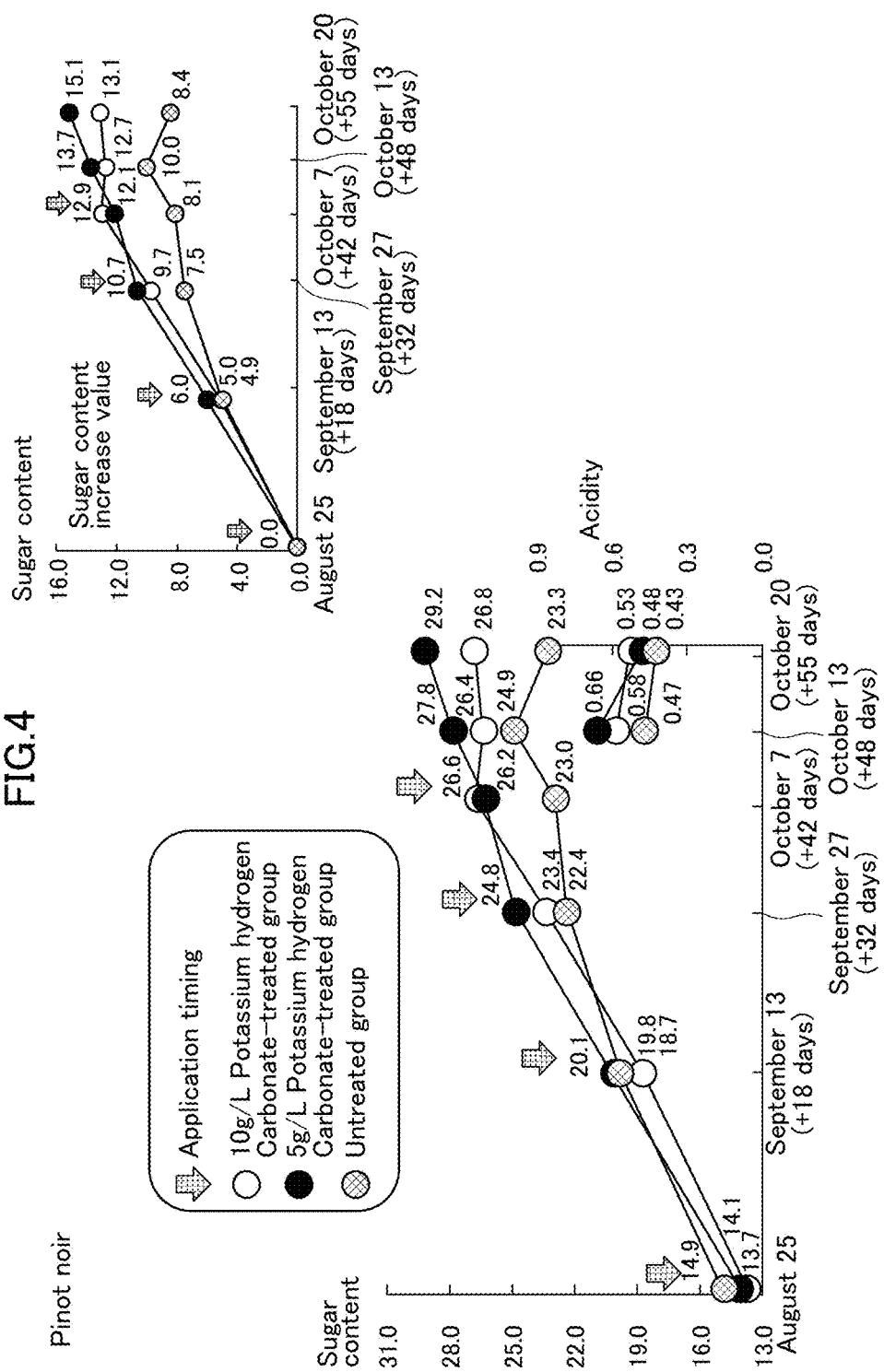
FIG. 4 is a graph showing changes in sugar content and acidity in a case where the agents for increasing a sugar content in a fruit of the present invention were applied to Pinot noir in Example 1.

Hereinafter, the present invention will be described in detail.

<<Agent for Increasing Sugar Content in Fruit>>

A first aspect of the present invention is an agent for increasing a sugar content in a fruit of a plant, comprising a compound represented by the formula MX as an active ingredient.

In the formula, M represents alkali metal ion or alkaline earth metal ion. The alkali metal ion is preferably potassium ion or sodium ion, and the alkaline earth metal ion is preferably magnesium ion or calcium ion.

Of these ions, M is preferably alkali metal ion, and is particularly preferably potassium ion or sodium ion.

In the formula, X represents carbonate ion, hydrogen carbonate ion, acetate ion, citrate ion, succinate ion, phosphate ion, hydrogen phosphate ion, or pyrophosphate ion. Of these ions, X is preferably carbonate ion, hydrogen carbonate ion, pyrophosphate ion, or acetate ion, more preferably carbonate ion, hydrogen carbonate ion, or pyrophosphate ion, and particularly preferably carbonate ion or hydrogen carbonate ion.

Note that the absolute numbers of ionic charges on M and X in the formula MX are arranged in such a manner as to be equal to each other. For example, when M is potassium ion ($K^+$), and X is carbonate ion ($CO_3^{2-}$), MX means $K_2CO_3$.

Examples of the compound represented by the formula MX include potassium hydrogen carbonate, sodium hydrogen carbonate, calcium hydrogen carbonate, magnesium hydrogen carbonate, potassium carbonate, sodium carbonate, calcium carbonate, magnesium carbonate, potassium acetate, sodium acetate, calcium acetate, magnesium acetate, tripotassium phosphate, trisodium phosphate, dipotassium hydrogen phosphate, disodium hydrogen phosphate, tetrapotassium pyrophosphate, tetrasodium pyrophosphate, potassium citrate, sodium citrate, potassium succinate, sodium succinate, and the like. Of these compounds, preferred are potassium hydrogen carbonate, sodium hydrogen carbonate, potassium carbonate, sodium carbonate, potassium acetate, and sodium acetate, more preferred are potassium hydrogen carbonate, sodium hydrogen carbonate, potassium carbonate, and sodium carbonate, and particularly preferred are potassium hydrogen carbonate and potassium carbonate. Potassium carbonate is the most preferable.

To the agent for increasing a sugar content in a fruit of the present invention, it is preferable to add a vegetable oil and/or fat, in addition to the compound represented by the formula MX. The inclusion of the vegetable oil and/or fat increases the period for which the active ingredient adheres to the plant, enabling the active ingredient to act on the plant for a longer period.

The vegetable oil and/or fat includes soybean oil, rapeseed oil, canola oil, sunflower oil, corn oil, olive oil, palm oil, palm kernel oil, coconut oil, castor oil, peanut oil, sesame oil, flaxseed oil, camellia oil, cottonseed oil, and safflower oil. Sunflower oil, soybean oil, safflower oil, and rapeseed oil are particularly preferable. One vegetable oil and/or fat may be used alone, or two or more of vegetable oils and/or fats may be used in combination.

When the vegetable oil and/or fat is used, the vegetable oil and/or fat is preferably added at a ratio of 1 to 30 parts by mass, and more preferably 3 to 25 parts by mass, relative to 100 parts by mass of the compound represented by the formula MX.

In the agent for increasing a sugar content in a fruit of the present invention, a surfactant may be used as an emulsifier and/or a spreader/sticker, if necessary.

The addition of the surfactant increases the period for which the active ingredient adheres to the plant, enabling the active ingredient to act on the plant for a longer period. The surfactant also acts as an emulsifier, and makes it easier to emulsify the vegetable oil and/or fat in water, when the agent for increasing a sugar content in a fruit of the present invention is diluted with water.

As the surfactant, any one of a nonionic surfactant, a cationic surfactant, and an anionic surfactant may be used. One surfactant may be used alone, or two or more surfactants may be used in combination. Of these surfactants, a nonionic surfactant and/or a cationic surfactant are preferable.

Preferred nonionic surfactants include polyoxyethylene alkyl ethers, polyoxyethylene alkylphenyl ethers (for example, polyoxyethylene nonylphenyl ether), polyoxyethylene polyoxypropylene ethers, polyoxyethylene alkyl esters, sorbitan fatty acid esters, polyoxyethylene sorbitan fatty acid esters, polyoxyethylene-polyoxypropylene block polymers, higher-fatty acid alkanolamides, and the like), and a polyoxyethylene alkyl ether or a polyoxyethylene sorbitan fatty acid ester is particularly preferable.

Preferred cationic surfactants include alkylamine salts, quaternary ammonium salts, and the like, and polyoxyethylene cocoamine is particularly preferable.

Preferred anionic surfactants include lignosulfonic acid salts (for example, calcium ligninsulfonate), alkylbenzenesulfonic acid salts (for example, sodium alkylbenzenesulfonates), alkylnaphthalenesulfonic acid salts (for example, sodium alkylnaphthalenesulfonates), higher-alcohol sulfates, higher-alcohol ether sulfates, dialkylsulfosuccinates, higher-fatty acid alkali metal salts, and the like.

In addition, specific examples of the preferred surfactants include polyoxyethylene cocoamine (SORPOL 7643, TOHO CHEMICAL INDUSTRY Co., Ltd.), polyoxyethylene alkyl ether (B-205, Riken Vitamin Co., Ltd.), polyoxyethylene sorbitan fatty acid ester (Sorbon T-20, TOHO CHEMICAL INDUSTRY Co., Ltd.), diglycerinmonooleate (RIKEMAL DO-100, Riken Vitamin Co., Ltd.), and the like.

It is also possible to use surfactants such as polyglycerin monooleates, glycerin fatty acid esters, sorbitan fatty acid esters, propylene fatty acid esters, higher-alcohol fatty acid esters, and ethylene oxide adducts thereof.

When the surfactant is used, the surfactant is added at a ratio of preferably 0.1 to 50 parts by mass, more preferably 1 to 30 parts by mass, and further preferably 1 to 10 parts by mass, relative to 100 parts by mass of the compound represented by the formula MX.

One surfactant may be used alone, or two or more surfactants may be used in combination.

The target plant is not particularly limited, as long as the plant bears fruit. The target plant is preferably grape, tomato (cherry tomato), apple, and Mikan (*Citrus unshiu*). Of these plants, grape is particularly preferable. As the grape, Chardonnay, Merlot, Cabernet Sauvignon, Pinot noir, Barikan, Steuben, Red Globe, Crimson, Sauvignon Blanc, Riesling, and Koshu are preferable. The agent can be used also for table grapes varieties, when the table grapes varieties are used for processing or fermentation. Examples of the table grapes varieties include Pione, Delaware, Aki Queen, Gold, Niagara, Hakuho, Unicorn, Red Queen, and the like.

Moreover, also when the agent for increasing a sugar content in a fruit of the present invention is used for fruit plants other than grape, various sweet fruit wines can be produced as in the case of grape.

The agent for increasing a sugar content in a fruit of the present invention is capable of increasing a sugar content in a fruit by a simple method, without being restricted by a cultivation area or a climatic environment. Accordingly, in regions of insufficient sugar content, the present invention makes it possible to obtain a fruit with a necessary sugar content. In addition, the present invention also makes it possible to obtain a fruit with an increased sugar content, when applied to a fruit with a normal sugar content. Accordingly, for example, in the cases of wines, wines with desired sugar contents can be produced ranging from an ordinary wine to a wine corresponding to a noble rot wine.

<<Method for Increasing Sugar Content in Fruit>>

A second aspect of the present invention is a method for increasing a sugar content in a fruit of a plant, the method comprising applying the above-described agent for increasing a sugar content in a fruit to the plant.

Regarding the agent for increasing a sugar content in a fruit, the compound represented by the formula MX is preferably applied to the plant at a concentration of 1 g/L to 100 g/L. The concentration is more preferably 1 to 50 g/L, and particularly preferably 3 to 20 g/L. When an application solution is prepared by diluting, with water, a preparation (a solution composition containing the compound represented by the formula MX and the vegetable oil and/or fat but substantially not containing water) of the agent for increasing a sugar content in a fruit, it is only necessary to prepare the application solution such that the compound represented by the formula MX can be contained within the above-describe range. The preparation of the agent for increasing a sugar content in a fruit contains the vegetable oil and/or fat in an amount of preferably 1 to 30 parts by mass, and more preferably 3 to 25 parts by mass, relative to 100 parts by mass of the compound represented by the formula MX.

In addition, when the above-described diluted agent for increasing a sugar content in a fruit is applied to a plant, the compound represented by the formula MX is applied in an amount of preferably 1 to 100 kg/ha, more preferably 1 to 50 kg/ha, further preferably 1 to 30 kg/ha, and particularly preferably 4 to 30 kg/ha.

The application period varies depending on the desired sugar content, the number of times of the application, and the like. In general, the application is preferably conducted in a period from 2 months, 1.5 months, 1 month, or 0 months (i.e., on an expected harvest date or a harvest date) before the expected harvest date or the harvest date to 1 month, 1.5 months, or 2 months after the expected harvest date or the harvest time. A longer application period increases the sugar content more. However, the agent for increasing a sugar content in a fruit of the present invention can remarkably increase the sugar content in the fruit, even when the above-described application period is short.

In Description and Claims, the "harvest date" means the date on which the fruit is actually harvested, and the "expected harvest date" means the date on which the fruit is expected to be harvested. Hence, the expression "to 1 month, 1.5 months, or 2 months after the expected harvest date or the harvest date" means not only the period to 1 month, 1.5 months, or 2 months after the harvest date in a case where the fruit is actually harvested, but also the period to 1 month, 1.5 months, or 2 months after the expected harvest date in a case where the fruit is not harvested on the expected harvest date, but is allowed to continue to grow. In other words, no matter whether the fruit is yet to be harvested or already harvested, the agent for increasing a sugar content in a fruit of the present invention can promote the evaporation of water from the fruit and increase the sugar content in the fruit.

The expected harvest date varies depending on the kind of the fruit. In the case of the present invention, the expected harvest date refers to a harvest time of the fruit estimated by agriculture workers for that season. For example, the actual expected harvest date of grape is determined considering the appearance and the taste, as well as the acid and sugar concentrations, the astringency of the seeds, and the like. Meanwhile, the expected harvest dates of apple, Mikan, tomato, and the like are also determined, as appropriate, based on the appearance and the taste.

The agent may be applied to the entire plant body, or may be directly applied only to the fruit of the plant. The direct application to the fruit is preferable from the economical viewpoint. In addition, when the agent is applied after harvest, it is only necessary to directly apply the agent to the fruit of the plant.

The number of times of the application of the agent for increasing a sugar content in a fruit to the plant may be only one, and is preferably about two to eight, and more preferably about three to six, from the viewpoint of the sugar content-increasing effect.

When the number of times of the application is one, it is only necessary to apply the agent once during the above-described application period.

Meanwhile, when the agent is applied to the plant two or more times, the interval of the application is not particularly limited, and is preferably 3 days to 2 weeks, and further preferably 5 days to 10 days.

<<Method for Producing Fruit Wine>>

A third aspect of the present invention is a method for producing a fruit wine including grape wine, the method comprising using, as a raw material, a fruit, especially fruit of grape, to which the above-described agent for increasing a sugar content in a fruit has been applied.

In the present invention, a method which is the same as a conventionally employed method for producing a fruit wine may be employed, except that a fruit to which the agent for increasing a sugar content in a fruit has been applied is used as a raw material. Specifically, the fruit wine is produced through steps such as crushing, destemming, pressing, fermentation, and barrel aging.

The fruit wine obtained by the method for producing a fruit wine of the present invention has a high sugar content, because the fruit to which the agent for increasing a sugar content in a fruit has been applied is used as a raw material. Consequently, the obtained fruit wine has a very sweet and mellow flavor. Accordingly, for example, in a case of grape wine, a desired wine ranging from a ordinary wine to a noble rot wine can be produced at will by using fruit of grape having a sugar content suitable for the need.

<<Method for Producing Dried Grape>>

A fourth aspect of the present invention is a method for producing dried grape, comprising the step of adding (applying) a compound represented by the formula MX to grape.

In the formula, M and X are the same as M and X in the agent for increasing a sugar content in a fruit of the first aspect.

In addition, in the method of the present invention, other components may be added together with the compound represented by the formula MX. Examples of the other components include the same components as those described in the first aspect.

The timing of the addition may be before harvest of the grape, or after harvest of the grape. The timing of the addition is preferably within a period from 2 months, 1.5 months, 1 month, or 0 months before the expected harvest date or the harvest date of the grape to 1 month, 1.5 months, or 2 months after the expected harvest date or the harvest date. In addition, when the compound is added to the grape after harvest, the compound may be added to the grape before drying in the sun, or during the drying in the sun.

The number of times of the addition is not particularly limited, and the compound may be added, for example, 1 to 10 times, preferably 2 to 8 times, and more preferably 3 to 6 times. The interval of the addition is not particularly limited, either, and, for example, the compound can be added at intervals of 1 day to 1 week.

The concentration and the added amount of the compound at the addition may be the same as the concentration and the application amount described in the second aspect.

In general, dried grape is produced as follows. Specifically, harvested grape is dried in the sun for 2 to 3 weeks. After the water content in the raisin reached approximately 16% in the third week, the fruit is wrapped with a paper tray, and is left for further 2 to 3 days to achieve an uniform water distribution. Hence, the production of raisin requires time and labor during the period from the cutting of the grape to the completion of the drying in the sun. However, the use of the method of the present invention makes it possible to dry in advance the grape kept on vines, without cutting the grape from the vines. Hence, the time taken by the production of dried grape can be reduced to a great extent. In addition, also in a case where grape is dried in the sun, the use of the method of the present invention can increase the amount of water transpiration, and can make the time for drying the fruit of grape shorter than a conventional case. Moreover, the use of the method also can increase the concentration of amino acids contained in the raisin.

<<Agent Against Physiological Plant Disorder Caused by Calcium Deficiency>>

A fifth aspect of the present invention is an agent for preventing and/or treating a physiological plant disorder caused by calcium deficiency, the agent comprising a compound represented by the formula MX as an active ingredient.

In the formula, M and X are the same as M and X in the agent for increasing a sugar content in a fruit of the first aspect.

The agent of the present invention may comprise other components besides the compound represented by the formula MX. Examples of the other components include the components described in the first aspect.

The target plant may be cherry, lettuce, celery, cabbage, nappa cabbage, strawberry, cucumber, tomato, eggplant, bell pepper, or the like.

The physiological plant disorder caused by calcium deficiency may be water-soaked symptom, tipburn, heart rot symptom (lettuce, nappa cabbage, and the like), blossom-end rot symptom (tomato, eggplant, and bell pepper), or curvature symptom.

The concentration and the application amount of the agent of the present invention may be the same as the concentration and the application amount described in the second aspect.

The timing of the application, the number of times of the application, and the like may be adjusted according to the timing in which the physiological plant disorder caused by calcium deficiency occurs, the symptom of the physiological plant disorder, and the like. For example, in a case of lettuce or celery, the physiological plant disorder (calcium deficiency symptom) caused by calcium deficiency occurs because of the change in meteorological conditions or vigor of the plant occurring from summer to fall. Hence, the agent may be applied from summer to fall about 1 to 10 times at intervals of several days to several weeks.

Although not clear, a reason why physiological disorders caused by calcium deficiency can be prevented and/or treated by applying the agent of the present invention is presumably as follows. Specifically, the application of the agent of the present invention to the plant results in increase in the amount of transpiration from the plant, and consequently increases the amount of water absorbed through the roots. In general, calcium (ions) is hardly absorbed through the surfaces of the leaves, but is taken together with water, when the roots absorb water. Presumably for this reason, the plant can be easily recovered from the calcium deficiency by increasing the amount of transpiration.

<<Agent for Preventing Fruit Cracking>>

A sixth aspect of the present invention is an agent for preventing fruit cracking of a fruit of a plant, the agent comprising a compound represented by the formula MX as an active ingredient.

In the formula, M and X are the same as M and X in the agent for increasing a sugar content in a fruit of the first aspect.

The agent for preventing fruit cracking of the present invention may comprise other components besides the compound represented by the formula MX. Examples of the other components include the components described in the first aspect.

The target plant is not particularly limited, as long as the plant is known to undergo fruit cracking. Examples of the target plant include cherry, grape, tomato, plum, peach, melon, watermelon, apple, pear, Mikan, and the like.

The concentration and the application amount of the agent of the present invention may be the same as the concentration and the application amount described in the second aspect.

The timing of the application, the number of times of the application, and the like may be adjusted according to the timing in which the fruit cracking occurs. In general, fruit cracking occurs near the expected harvest date of the fruit of the plant. Hence, for example, the agent may be applied 1 to 10 times at intervals of several days to several weeks in a period from 2 months, 1.5 months, 1 month, or 0.5 months before the expected harvest date to the harvest date.

Conventionally, as a countermeasure for prevention of the fruit cracking, extremely laborious methods such as cultivation under a rain shelter have been employed. However, even if the conventional countermeasure is used, the fruit cracking occurs in valley portions or edge portions of the rain shelter for cultivation, or because of blows of rain, sudden rainfall after drying, or the like. When a fruit of a plant cracks, the fruit becomes valueless on the market. Hence, it is desirable that the fruit cracking be prevented more reliably. The use of the agent for preventing fruit cracking of the present invention makes it possible to more reliably prevent fruit cracking of a fruit of a plant, without using the above-described conventional method, or in combination with the above-described conventional method.

Although not clear, a mechanism in which the agent for preventing fruit cracking of the present invention prevents the fruit cracking is presumably as follows. Specifically, the agent for preventing fruit cracking of the present invention increases the amount of transpiration of water from a fruit of a plant. Hence, the water content in the fruit decreases, and the skin of the fruit gets wrinkles. Presumably, as a result of this, the skin of the fruit becomes resistant to rupture, so that the fruit cracking can be prevented, even when the fruit receives an impact because of rainfall or the like.

<<Agent for Maintaining Acidity and/or pH of Fruit of Plant>>

A seventh aspect of the present invention is an agent for maintaining acidity and/or pH of a fruit of a plant, the agent comprising a compound represented by the formula MX as an active ingredient.

In the formula, M and X are the same as M and X in the agent for increasing a sugar content in a fruit of the first aspect.

The maintaining agent of the present invention may comprise other components besides the compound represented by the formula MX. Examples of the other components include the components described in the first aspect.

Examples of the target plant include grape, tomato, and *citrus* fruits (Mikan etc.).

The concentration, the application amount, application timing, application method, and the like of the maintaining agent of the present invention may be the same as the concentration, application amount, application timing, application method, and the like described in the second aspect. In addition, the timing of the application is preferably before the harvest of the fruit of the plant, and is more preferably a time point which is in a period from 2 months, 1.5 months, 1 month, or 0 months before the expected harvest date to 1 month, 1.5 months, or 2 months after the expected harvest date and which is before the harvest of the fruit of the plant.

The fruit of the plant to which the maintaining agent of the present invention is applied can retain the acidity in a high state and the low pH for a longer period than a fruit of the plant to which the maintaining agent is not applied. Hence, such fruit is suitable for production of a wine with a high sugar content and a high acidity.

<<Agent for Increasing Concentration of Amino Acid>>

An eighth aspect of the present invention is an agent for increasing a concentration of an amino acid contained in a plant body (fruit, leaf, stem, and/or root of the plant), the agent comprising a compound represented by the formula MX as an active ingredient.

In the formula, M and X are the same as those in the agent for increasing a sugar content in a fruit of the first aspect.

The agent for increasing a concentration of an amino acid of the present invention may comprise other components besides the compound represented by the formula MX. Examples of the other components include the same components as those described in the first aspect.

The target plant is not particularly limited, and examples thereof include grape, tomato, lettuce, wheat, rice plant, cabbage, soybean, potato, cabbage, spinach, and the like.

The concentration, application amount, application timing, application method, and the like of the agent for increasing a concentration of an amino acid of the present invention may be the same as the concentration, application amount, application timing, application method, and the like described in the second aspect.

The agent for increasing a concentration of an amino acid of the present invention is capable of increasing the total mass of all the amino acids contained in a plant body. Especially, the amounts of arginine, glutamine ($GluNH_2$), ornithine, alanine, citrulline, asparagine ($AspNH_2$), aspartic acid, glutamic acid, a-ABA, threonine, serine, lysine, histidine, glycine, and phenylalanine can be remarkably increased, and particularly the amounts of arginine, glutamine ($GluNH_2$), ornithine, and alanine can be increased. Arginine is the most remarkably increased amino acid.

Although not clear, a reason why the agent for increasing a concentration of an amino acid of the present invention increases the amino acid concentration is presumably as follows. Specifically, the ratio of the amino acid concentration in the fruit of the plant treated with the compound of the present invention to the amino acid concentration contained in fruit of an untreated plant is higher than the ratio of the sugar content in the fruit of the plant treated with the compound of the present invention to the sugar content of the fruit of the untreated plant. Hence, it can be understood that the increase in amino acid concentration cannot be explained only by concentration of the amino acids by transpiration. Presumably, the application of the compound of the present invention increases the amounts of amino acids themselves by the action of some mechanism other than the transpiration of water.

EXAMPLES

Example 1

Test of Increase in Sugar Content in Fruit by Application of Agent for Increasing Sugar Content in Fruit To the entire vines including leaves and stems of grapes (varieties: Chardonnay, Pinot noir, Merlot, and Cabernet Sauvignon, 7 years old) in a farm field, an agent (containing Sorbon T-20 as a spreader/sticker at a concentration of 200 µL/L) for increasing a sugar content in a fruit diluted with water to have a potassium hydrogen carbonate concentration of 5 g/L or 10 g/L was applied in a sufficient amount (3000 L/ha (in this case, the amount of potassium hydrogen carbonate was 15 kg/ha for the 5 g/L sample or 30 kg/ha for the 10 g/L sample) each time. The application was repeatedly conducted at intervals of approximately 2 weeks or approximately 1 week as shown in FIGS. 1 to 4. The sugar concentration in the fruit was measured over time. As a control, unapplied vines were provided. The sampling was started before the first application, and a sample was collected before each application, and measured for the sugar content. Three vines were used for each treated group. Note that the expected harvest dates were September 20 for Chardonnay, October 10 for Merlot, October 20 for Cabernet Sauvignon, and September 30 for Pinot noir.

For the measurement of the sugar content, three clusters were taken from each of the treated vines on each of the dates of measurement, and the juice was squeezed and measured for the Brix sugar content (%) with a refractometer for sugar content (manufactured by Atago Co., Ltd.). Likewise, the acidity (%) was also measured with an acidity meter (manufactured by Atago Co., Ltd.).

FIGS. 1 to 4 show the results. Note that, in each of FIGS. 1 to 4, the numeric values on the vertical axis indicate the sugar content or the acidity in percentage (%).

As can be seen from FIGS. 1 to 4, in each of the cases of Chardonnay, Merlot, Cabernet Sauvignon, and Pinot noir, the fruit of grape to which potassium hydrogen carbonate was applied at 5 g/L and the fruit of grape to which potassium hydrogen carbonate was applied at 10 g/L underwent greater increase in sugar content than the untreated fruit of grape. In general, decrease in acidity is observed with the increase in sugar content. In contrast, the acidity in this test was kept equal to or slightly higher than that of the untreated group.

Example 2

Test of Increase in Sugar Content in Fruit by Application of Agent for Increasing Sugar Content in Fruit to which Vegetable Oils were Added The vegetable oils, surfactants, and emulsifiers listed in Table 1 below were mixed with each other, and melted by heating at approximately 60° C. Next, the active ingredients listed in Table 1 were added to the obtained mixture liquids, followed by sufficient mixing. Thus, preparations of agents for increasing a sugar content in a fruit containing sodium hydrogen carbonate or potassium hydrogen carbonate were prepared (the preparations are also referred to as a sodium hydrogen carbonate preparation and a potassium hydrogen carbonate preparation, respectively). Note that parts in the table represents parts by mass.

TABLE 1

|  | Sodium hydrogen carbonate preparation | Potassium hydrogen carbonate preparation |
|---|---|---|
| Active ingredient | Sodium hydrogen carbonate (100 parts) | Potassium hydrogen carbonate (100 parts) |
| Vegetable oil and/or fat | Sunflower oil (22.4 parts) Soybean oil (2.24 parts) | Sunflower oil (22.4 parts) Soybean oil (2.24 parts) |
| Surfactant | Polyoxyethylene cocoamine (SORPOL 7643, manufactured by TOHO CHEMICAL INDUSTRY Co., Ltd.) (2 parts) Polyoxyethylene alkyl ether (B-205, manufactured by Riken Vitamin Co., Ltd.) (0.56 parts) Polyoxyethylene sorbitan monolaurate (product name: Sorbon T-20, manufactured by TOHO CHEMICAL INDUSTRY Co., Ltd.) (0.56 parts) Diglycerin monooleate (RIKEMAL DO-100, manufactured by Riken Vitamin Co., Ltd.) (2.24 parts) | Polyoxyethylene cocoamine (SORPOL 7643, manufactured by TOHO CHEMICAL INDUSTRY Co., Ltd.) (2 parts) Polyoxyethylene alkyl ether (B-205, manufactured by Riken Vitamin Co., Ltd.) (0.56 parts) Polyoxyethylene sorbitan monolaurate (product name: Sorbon T-20, manufactured by TOHO CHEMICAL INDUSTRY Co., Ltd.) (0.56 parts) Diglycerin monooleate (RIKEMAL DO-100, manufactured by Riken Vitamin Co., Ltd.) (2.24 parts) |

Each of the prepared preparations of the agents for increasing a sugar content in a fruit were diluted with water to have a concentration of sodium hydrogen carbonate or potassium hydrogen carbonate of 10 g/L. Thus, application solutions were prepared. The diluted solutions were each applied in a sufficient amount (1000 L/ha) each time to only fruits of grapes (varieties: Pinot noir, approximately 7 years old) in a farm field. The application was started 3 weeks (September 13) before the expected harvest date (October 4), and conducted five times in total at intervals of approximately 1 week (dates of application: September 13, September 20, September 27, October 4, and October 11). In addition, an untreated group was provided as a control. The sampling was started before the first application, and a sample was collected before each application and measured for the sugar content.

For the measurement of the sugar content, three clusters were taken from each of the treated vines, and the juice was squeezed and measured for the Brix sugar content with a refractometer for sugar content (manufactured by Atago Co., Ltd.).

Figure 5:
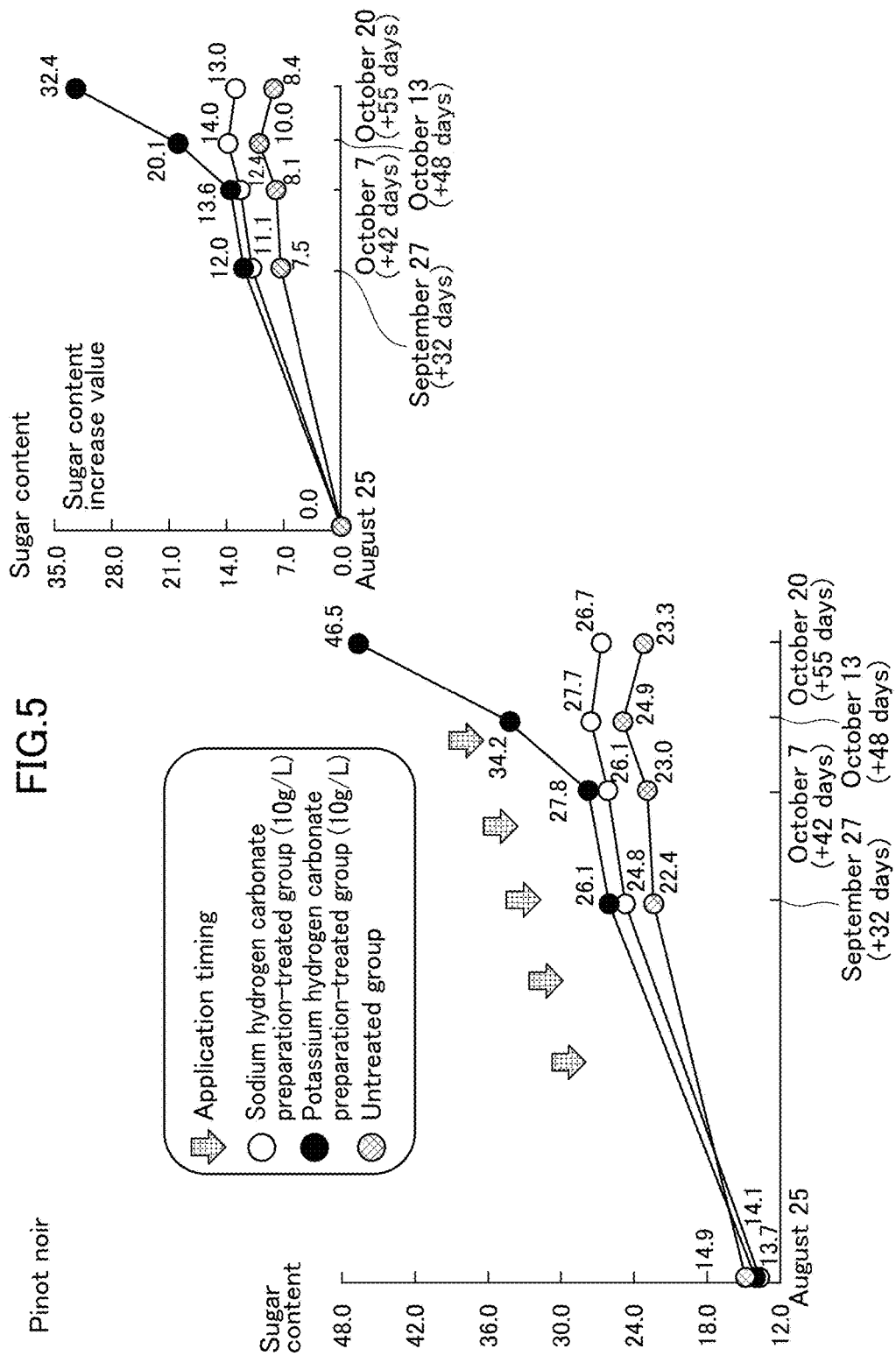
FIG. 5 is a graph showing changes in sugar content in a case where agents for increasing a sugar content in a fruit of the present invention (to which vegetable oils were added) were applied to Pinot noir in Example 2.

FIG. 5 shows the results. Note that each numeric value on the vertical axis in FIG. 5 represents the sugar content (%) or the acidity (%).

As can be seen from FIG. 5, the sugar contents in the fruit of grape of the group for which the potassium hydrogen carbonate preparation was used and the group for which the sodium hydrogen carbonate preparation was used were remarkably increased in comparison with that of the untreated group after the start of the application.

In addition, Example 2 shows by what degree the potassium hydrogen carbonate preparation to which the vegetable oils and the like were added increased the sugar content of Pinot noir. On the other hand, Example 1 (FIG. 4) shows by what degree the potassium hydrogen carbonate to which no vegetable oil or the like was added increased the sugar content of Pinot noir, which was the same as in Example 2. The results shown in FIG. 4 and the results shown in FIG. 5 cannot be simply compared with each other, because the number of times of the application was different. However, from the results of the two, it can be seen that the sugar content increased more after the expected harvest time (on October 13 and October 20) in the case where the mixture of potassium hydrogen carbonate with the vegetable oils and the like was used than in the case where no vegetable oil or the like was mixed. The results above suggest that the addition of a vegetable oil and the like to potassium hydrogen carbonate further enhances the action of potassium hydrogen carbonate to increase a sugar content in a fruit of a plant.

Example 3

Test for Evaluating Amount of Transpiration and Degree of Increase in Sugar Content in Fruit As can be seen from the results of Examples 1 and 2, the application of the agents for increasing a sugar content in a fruit of the present invention increased the sugar content in the fruit. However, it was not clear why the agent for increasing a sugar content in a fruit of the present invention increases the sugar content in the fruit. The action to increase the sugar content of grape by the noble rot fungus is caused by melting of a waxy material in the skin of the fruit by the noble rot fungus and resultant evaporation of water in the fruit. Accordingly, also in the case of the agent for increasing a sugar content in a fruit of the present invention, it could be considered that the transpiration of water in the fruit may be associated with the increase in sugar content. Therefore, investigation was made by the following experiment as to the relationship between the amount of water transpired and the increase in sugar content in the fruit in a case where an agent for increasing a sugar content in a fruit of the present invention was applied.

<Method>

Agents for increasing a sugar content in a fruit (containing Sorbon T-20 as a spreader/sticker at a final concentration of 200 µL/L) diluted with water to contain one of the compounds listed in Table 2 as an active ingredient at a concentration of 10 g/L were each applied to harvested fruit of grape (variety: Barikan) purchased on the market. The fruit of grape was maintained in an air-conditioned greenhouse (temperature: 25° C.), and measured for the mass over time. The sugar content of the fruit was measured before the application and 8 days after the application with a sugar content meter. Next, on the assumption that the change in the mass of the fruit was entirely due to the change in water content, calculated values of the amount of decrease in mass and the sugar content on the date (June 2) of the application were determined from the sugar content eight days later by using the following calculation formula.

(Calculated as follows: the sugar content (%) calculated value))=the sugar content (%) before application×the mass (g) on the date of application/the mass (g) on the date of measurement))

Figure 6:
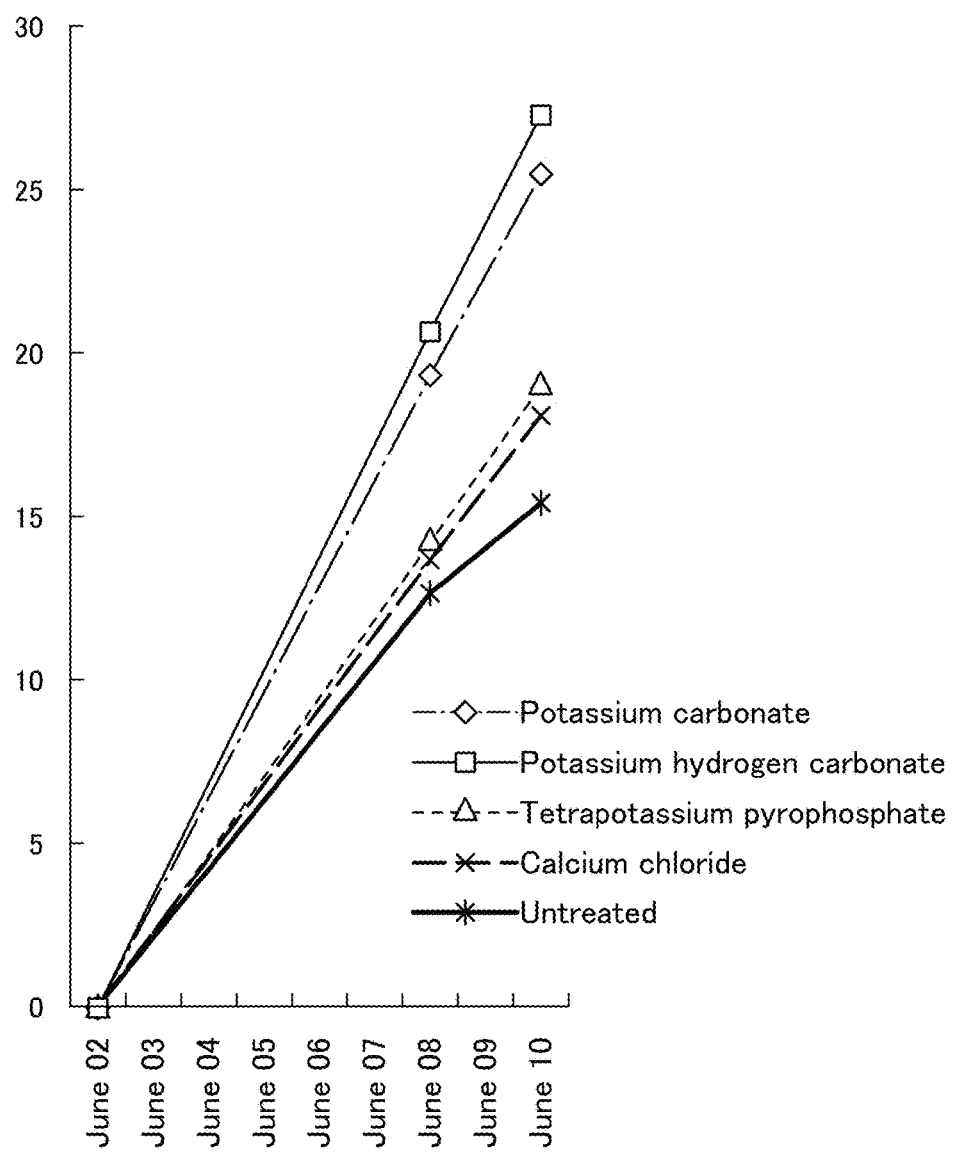
FIG. 6 is a graph showing the decrease ratio of the mass of fruit of grape achieved by agents for increasing a sugar content in a fruit of the present invention in Example 3.
Figure 7:
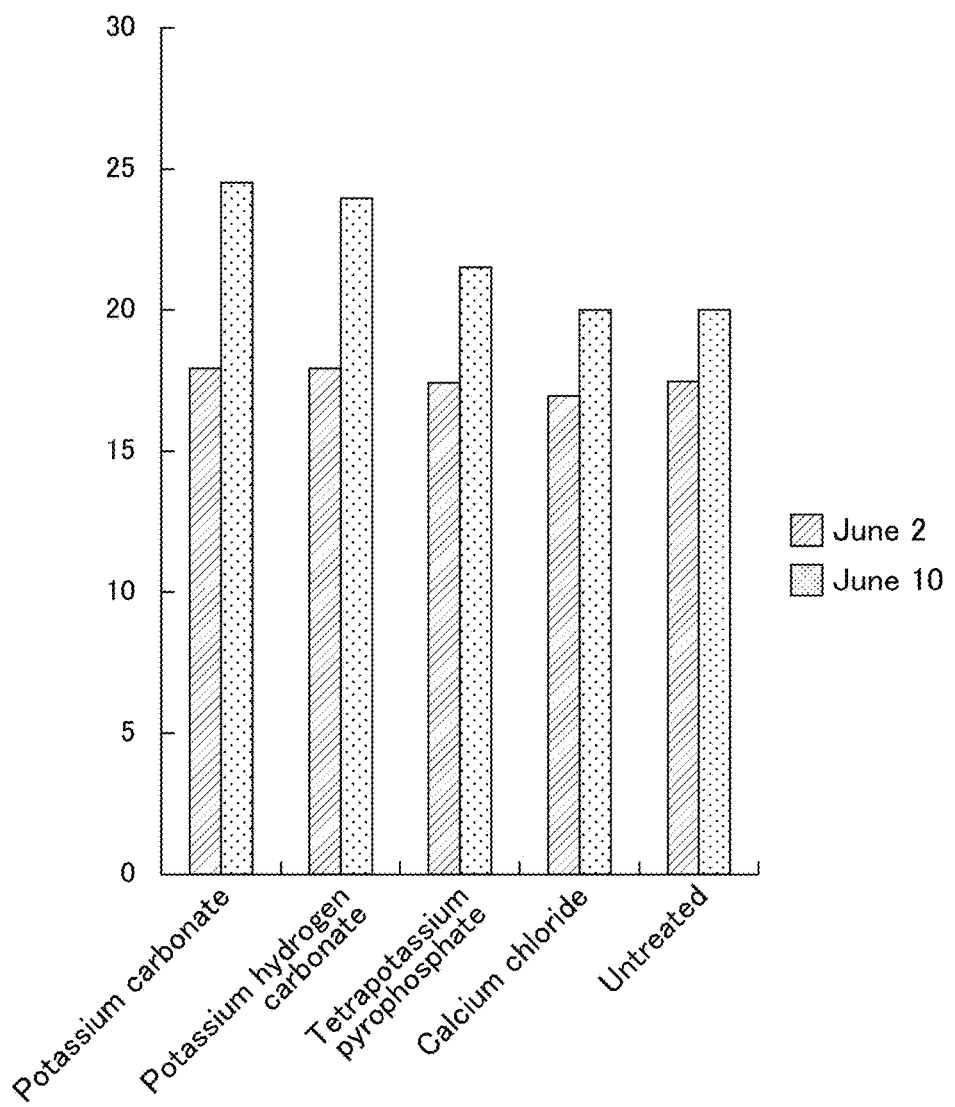
FIG. 7 is a graph in which comparisons are made between the sugar content (%) in fruit of grape on the date of the application (June 2) and the sugar content (%) in fruit of grape 8 days (June 10) after application of each agent for increasing a sugar content in a fruit of the present invention in Example 3.
Figure 8:
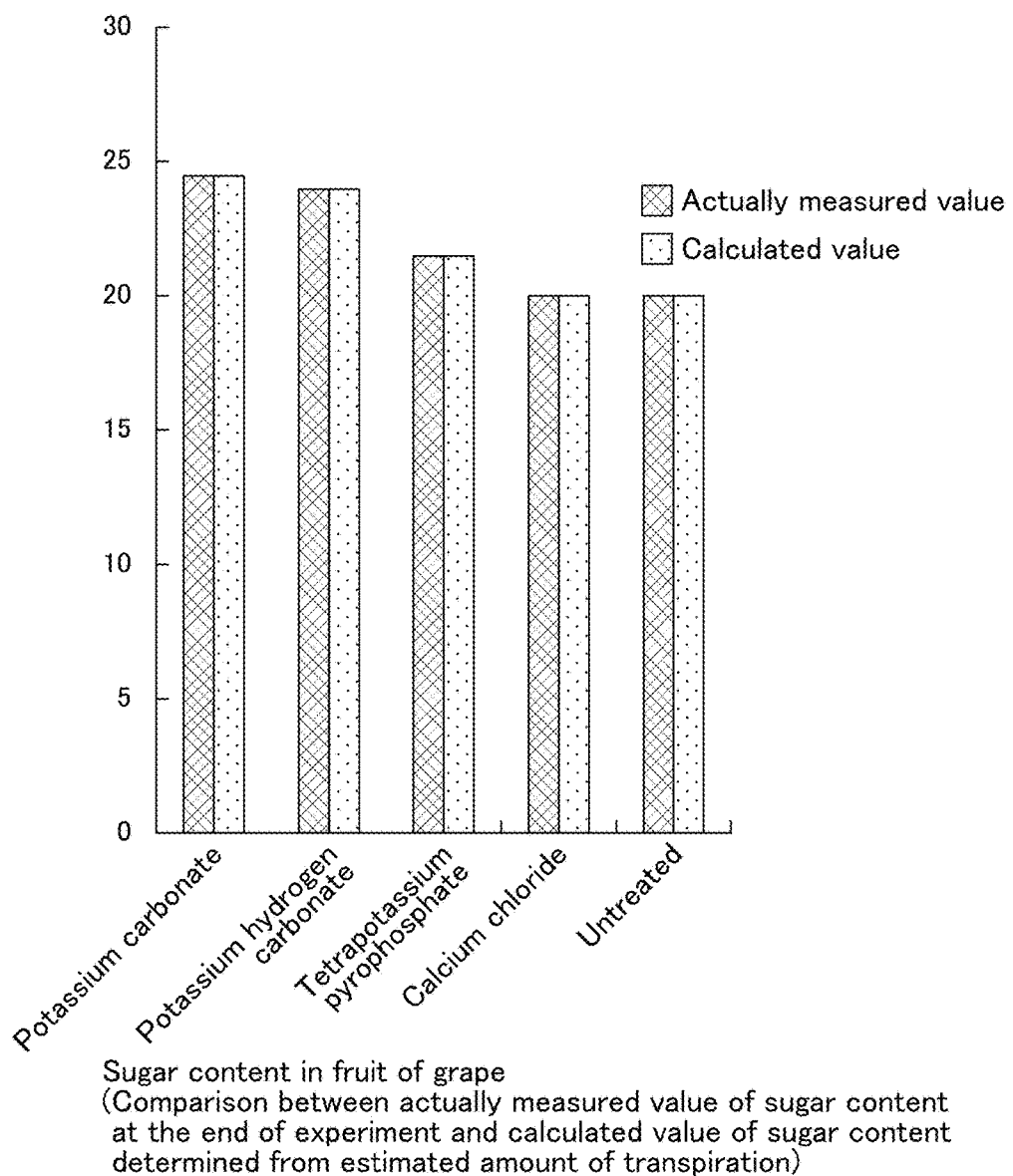
FIG. 8 is a graph in which the sugar content (%) in fruit of grape 8 days (June 10) after each agent for increasing a sugar content in a fruit of the present invention was applied in Example 3 was compared between the actually measured value (left) and the calculated value (right).

The calculated value of the sugar content was compared with the actually measured value of the sugar content. Table 2 and FIGS. 6 to 8 show the results. (Application: Jun. 2, 2011)

Note that the vertical axis in FIG. 6 represents the amount (g) of decrease in mass of the fruit of grape on each date of measurement per 100 g of the fruit of grape on the date of application (in other words, the ratio (%) of decrease in mass of the fruit of grape on each date of measurement).

TABLE 2

|  | Date of application (Jun. 2) | | 6 days later (Jun. 8) Mass (g) | 8 days later (Jun. 10) | | |
|---|---|---|---|---|---|---|
|  | Mass (g) | Sugar content (%) | | Mass (g) | Sugar content (%) Actually measured value | Calculated value |
| 1. Potassium carbonate | 100 | 18.0 | 80.7 | 74.5 | 24.5 | 24.2 |
| 2. Potassium hydrogen carbonate | 100 | 18.0 | 79.4 | 72.7 | 24.0 | 24.8 |
| 3. Tetrapotassium pyrophosphate | 100 | 17.5 | 85.7 | 80.9 | 21.5 | 21.6 |
| 4. Calcium chloride | 100 | 17.0 | 86.3 | 81.9 | 20.0 | 20.8 |
| 5. Untreated group | 100 | 17.5 | 88.3 | 84.6 | 20.0 | 20.7 |

<Result 1>

A comparison among potassium carbonate, potassium hydrogen carbonate, tetrapotassium pyrophosphate, calcium chloride, and the untreated group shows that potassium carbonate was the best in terms of the action to increase the sugar content in the fruit of grape, followed by potassium hydrogen carbonate and tetrapotassium pyrophosphate in this order. The ratio of increase in sugar content achieved by calcium chloride was almost the same as that of the untreated group.

<Result 2>

The masses of the fruits of the group treated with potassium carbonate, potassium hydrogen carbonate, and tetrapotassium pyrophosphate decreased in 8 days from June 2 to June 10 by 25.56%, 27.3%, and 19.1%, respectively (Table 2). With the decrease, the sugar contents, which were initially 18%, 18%, and 17.5%, increased to 24.5%, 24%, and 21.5%, respectively (actually measured values). When the sugar contents are calculated on the assumption that the decrease in the mass of the fruit was attributable to the loss of water, the calculated values are 24.2%, 24.8%, and 21.6%, respectively, which are in extremely good agreement with the actually measured values.

In each of the treated groups, the sugar content calculated on the assumption that the decrease in the mass of the fruit was attributable to the loss of water was almost the same as the actually measured value. Hence, it is conceivable that the decrease in mass of the fruit was due to transpiration of water. In other words, it is conceivable that the agent for increasing a sugar content in a fruit of the present invention increased the sugar content in the fruit by causing transpiration of water in the fruit.

Tests for Indirectly Evaluating Action to Increase Sugar Content in Fruit

Examples 4 to 9

From the results of Example 3, it was found that the increase in sugar content in a fruit achieved by the agent for increasing a sugar content in a fruit of the present invention was an increase in sugar content achieved through decrease in mass of the fruit due to transpiration of water in the fruit. In this respect, indirect evaluations were made as to whether or not each compound has an action to increase a sugar content in a fruit by investigating the degrees of decrease in mass in various plants in the following Examples.

Example 4

An agent for increasing a sugar content in a fruit (containing Sorbon T-20 as a spreader/sticker at a final concentration of 200 µL/L) diluted with water to contain potassium hydrogen carbonate at 10 g/L was prepared. The mass of fruit of grape (variety: Steuben) purchased on the market was measured. Then, the prepared agent for increasing a sugar content in a fruit was applied by spraying to the fruit of grape. The fruit of grape was allowed to stand in an air-conditioned greenhouse (temperature: 25° C.), and the mass was measured over time (date of application: Feb. 7, 2011). In addition, as a control, the mass of untreated grape was measured on each of the dates of measurement in the same manner. Table 3 shows the results.

TABLE 3

Change (g) with time in mass of fruit per 100 g of fruit of grape on date of application (Feb. 7)

|  | Date of application (Feb. 7) | 1 day later (Feb. 8) | 2 days later (Feb. 9) | 3 days later (Feb. 10) | 7 days later (Feb. 14) |
|---|---|---|---|---|---|
| Treated with potassium hydrogen carbonate | 100 | 96.2 | 92.1 | 88.6 | 74.9 |
| Untreated | 100 | 96.7 | 93.4 | 90.5 | 79.9 |

In 7 days from the application, the mass of the fruit of grape of the untreated group decreased from 100 g to 79.9 g, whereas the mass of the fruit of grape treated with potassium hydrogen carbonate decreased to 74.9 g. Accordingly, on the assumption that the decrease in mass was entirely due to transpiration of water, 20 ml of water was lost per 100 g of the untreated grape, whereas approximately 25 ml of water was lost per 100 g of the grape treated with potassium hydrogen carbonate. In other words, it is conceivable that the treatment with potassium hydrogen carbonate increases the amount of transpiration from the fruit by about 25% in comparison with the untreated group.

The ratios of change in sugar content in the fruit calculated from the above-described values were as follows. Specifically, on the assumption that the sugar content in the fruit on the date of application was 15%, the sugar content of the untreated group 7 days later was 18.8%, whereas the sugar content of the group treated with potassium hydrogen carbonate was increased to 20.0%.

Example 5

Agents for increasing a sugar content in a fruit (containing Sorbon T-20 as a spreader/sticker at a final concentration of 200 μL/L) diluted with water to have the concentrations of potassium hydrogen carbonate shown in Table 4 were prepared. The mass of fruit of grape (variety: Red Globe) purchased on the market was measured. Then, the prepared agents for increasing a sugar content in a fruit were applied by spraying to the fruit of grape, which was then allowed to stand in an air-conditioned greenhouse (temperature: 25° C.). The mass of the fruit of grape was measured over time (date of application: Mar. 10, 2011). In addition, as a control, the mass of untreated grape was measured on each date of measurement in the same manner. Table 4 shows the results, and FIG. 9 shows the appearance of the grape on March 30 (FIG. 9 (a): application of potassium hydrogen carbonate (10 g/L), FIG. 9 (b): application of potassium hydrogen carbonate (5 g/L), FIG. 9(c): untreated). Note that the decrease ratio (cumulative, %) represents the percentage (%) of the mass decreased from the date of application to each of the dates of measurement, and the decrease ratio (%/day) represents the average ratio (%) of decrease in mass in a period between each of the dates of measurement and the preceding date of measurement (=(the mass (g) on the preceding date of measurement of each of the dates of measurement–the mass (g) on the date of measurement)/the mass (g) on the preceding date of measurement of the date of measurement/the number of days from the preceding date of measurement of the date of measurement to the date of measurement×100).

As shown in Table 4, the fruits to which potassium hydrogen carbonate was applied had higher ratios of decrease in mass than the untreated fruit. Accordingly, potassium hydrogen carbonate is capable of significantly increasing the sugar content in the fruit of Red Globe in comparison with the untreated case. In addition, the decrease ratio of mass was lower in the case where the concentration of potassium hydrogen carbonate was 5 g/L than in the case where the concentration was 10 g/L. Hence, it is conceivable that the sugar content can be increased more in the case of 10 g/L than in the case of 5 g/L.

Example 6

An agent for increasing a sugar content in a fruit (containing Sorbon T-20 as a spreader/sticker at a final concentration of 200 μL/L) diluted with water to have a potassium hydrogen carbonate concentration of 10 g/L was prepared. The mass of fruit of grape (variety: Red Globe) purchased on the market was measured. Then, the prepared agent for increasing a sugar content in a fruit was applied by spraying to the fruit of grape. Then, the fruit of grape was allowed to stand in an air-conditioned greenhouse (temperature: 25° C.), and the mass was measured over time (date of application: Apr. 27, 2011; dates of test: May 2, 2011, May 6, 2011, May 9, 2011, May 11, 2011, May 13, 2011, and May 16, 2011). In addition, as a control, the mass of untreated grape was measured on each date of measurement in the same manner.

On the basis of the measured mass, the estimated amount (cumulative value) of transpiration and the estimated amount of transpiration per day were calculated. The results are shown in Tables 5 and 6 and FIGS. 10 and 11.

Figure 10:
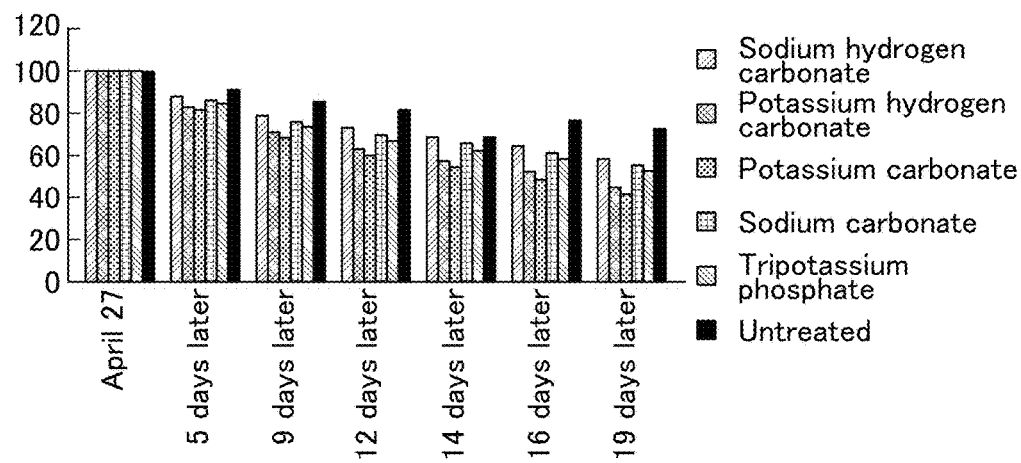
FIG. 10 is a graph showing the mass (g) of fruit on each date of measurement per 100 g of the fruit on the date of application in Example 6.
Figure 11:
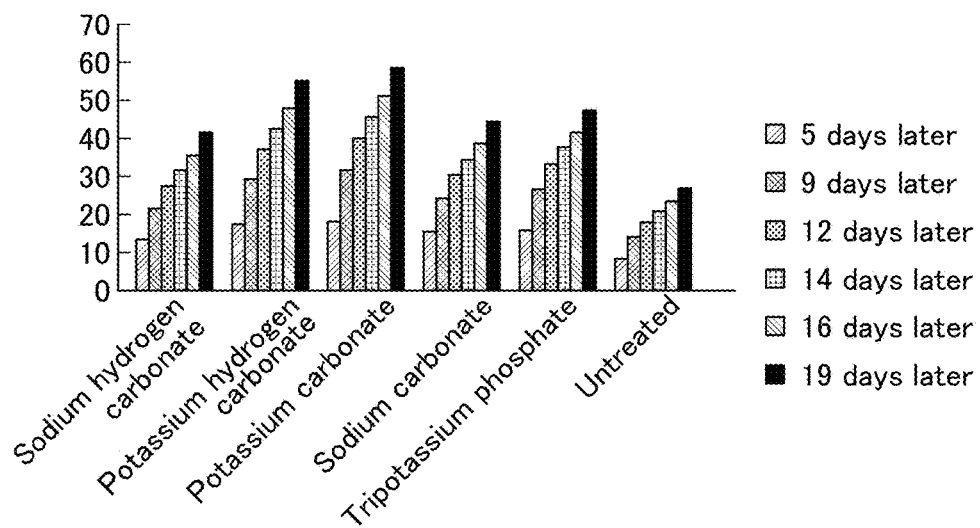
FIG. 11 is a graph showing the estimated amount (g) of transpiration on each date of measurement per 100 g of fruit on the date of application in Example 6.

Note that the vertical axis in FIG. 10 represents the mass (g) of the fruit of grape on each of the dates of measurement per 100 g of the fruit of grape on the date of application, and the vertical axis in FIG. 11 represents the estimated amount (g) of transpiration on each of the dates of measurement per 100 g of the fruit of grape on the date of application.

The estimated amount (g) of transpiration on each of the dates of measurement per 100 g of the fruit of grape on the date of application=(the mass (g) of the fruit of grape on the date of application–the mass (g) of the fruit of grape on the date of measurement)/the mass of the fruit of grape on the date of application×100

TABLE 4

| | | Mar. 10 | Mar. 11 | Mar. 14 | Mar. 15 | Mar. 16 | Mar. 18 | Mar. 22 | Mar. 23 | Mar. 24 | Mar. 30 |
|---|---|---|---|---|---|---|---|---|---|---|---|
| 1. Potassium hydrogen carbonate-1 (10 g/L) | Mass (g) | 200.5 | 194.8 | 177.2 | 171.4 | 166.5 | 157.4 | 141.3 | 136.3 | 132.5 | 109.7 |
| | Decrease ratio (cumulative %) | 0 | 2.9 | 11.6 | 14.5 | 17.0 | 21.5 | 29.5 | 32.0 | 33.9 | 45.3 |
| | Decrease ratio (%/day) | 0 | 2.9 | 3 | 3.3 | 2.9 | 2.7 | 2.5 | 3.6 | 2.8 | 2.9 |
| 2. Potassium hydrogen carbonate-2 (5 g/L) | Mass (g) | 240.4 | 234.1 | 216.7 | 211.4 | 206.7 | 197.8 | 182.4 | 177.3 | 173.5 | 149.4 |
| | Decrease ratio (cumulative %) | 0 | 2.6 | 9.9 | 12.1 | 14.0 | 17.7 | 24.1 | 26.3 | 27.8 | 37.8 |
| | Decrease ratio (%/day) | 0 | 2.6 | 2.5 | 2.5 | 2.2 | 2.1 | 2.0 | 2.8 | 2.2 | 2.3 |
| 3. Untreated-1 | Mass (g) | 212.2 | 206.9 | 193.1 | 188.8 | 185.3 | 178.7 | 167.3 | 163.7 | 161.0 | 143.8 |
| | Decrease ratio (cumulative %) | 0 | 2.5 | 9.0 | 11.0 | 12.7 | 15.8 | 21.1 | 22.8 | 24.1 | 32.1 |
| | Decrease ratio (%/day) | 0 | 2.5 | 2.2 | 2.2 | 1.9 | 1.8 | 1.8 | 2.2 | 1.7 | 1.8 |

TABLE 5

Mass (g) of fruit on each date of measurement per 100 g of fruit on date of application

|  | Apr. 27 | 5 days later | 9 days later | 12 days later | 14 days later | 16 days later | 19 days later |
|---|---|---|---|---|---|---|---|
| Sodium hydrogen carbonate | 100 | 87.6 | 78.3 | 72.7 | 68.5 | 64.4 | 58.5 |
| Potassium hydrogen carbonate | 100 | 82.6 | 70.5 | 62.8 | 57.4 | 52.1 | 44.7 |
| Potassium carbonate | 100 | 81.2 | 68.5 | 60 | 54.2 | 48.7 | 41.4 |
| Sodium carbonate | 100 | 85.9 | 75.9 | 69.7 | 65.4 | 61.3 | 55.5 |
| Tripotassium phosphate | 100 | 84.1 | 73.7 | 66.9 | 62.4 | 58.3 | 52.8 |
| Untreated | 100 | 91.6 | 85.8 | 82 | 69.2 | 76.6 | 72.8 |

TABLE 6

Estimated amount (g) of transpiration per 100 g of fruit on date of application

|  | 5 days later | 9 days later | 12 days later | 14 days later | 16 days later | 19 days later |
|---|---|---|---|---|---|---|
| Sodium hydrogen carbonate | 12.4 | 21.7 | 27.3 | 31.5 | 35.6 | 41.5 |
| Potassium hydrogen carbonate | 17.4 | 29.5 | 37.2 | 42.6 | 47.9 | 55.3 |
| Potassium carbonate | 18.8 | 31.5 | 40 | 45.8 | 51.3 | 58.6 |
| Sodium carbonate | 14.1 | 24.1 | 30.3 | 34.6 | 38.7 | 44.5 |
| Tripotassium phosphate | 15.9 | 26.3 | 33.1 | 37.6 | 41.1 | 47.4 |
| Untreated | 8.4 | 14.2 | 18 | 20.8 | 23.4 | 27.2 |

As can be understood from Tables 5 and 6 and FIGS. 10 and 11, the estimated amount of transpiration of the fruit of grape to which the sodium salt or potassium salt solution was applied increased in comparison with that of the untreated fruit. The largest estimated amount of transpiration was that of the fruit of grape to which the dilute aqueous solution of potassium carbonate was applied. The ratio of transpiration of the fruit of grape approximately 3 weeks later (19 days later) was 58.6%, and the mass decreased to 41.4% of the mass on the date of application. The second largest estimated amount of transpiration was that of the fruit of grape to which the dilute aqueous solution of potassium hydrogen carbonate was applied. The ratio of transpiration of the fruit of grape approximately 3 weeks later (19 days later) was 55.3%, and the mass of the fruit decreased to 44.7% of the mass on the date of application.

Specifically, it was shown that when a sodium or potassium salt solution was applied, the estimated amount of transpiration from fruit increased by about 1.6 to 2.0 times, and this increase was persistent. The estimated amount of transpiration was larger in the case of the potassium salt than in the case of the sodium salt. The estimated amount of transpiration of the fruit of grape to which the potassium carbonate solution was applied, which was the largest, was two times or more of that of the untreated fruit, and the mass decreased to approximately ½ of the mass on the date of application in 2 weeks. On the assumption that the sugar concentration in the fruit on April 27, which was the date of application, was 20% ("20/100" (calculated by using a mass of sugar of 20 g and a total mass of 100 g)), it was suggested that the sugar concentration exceeded 48% ("20/41.4" (calculated by using a mass of sugar of 20 g and a total mass of 41.4 g)) 2 weeks later.

Example 7

Agents for increasing a sugar content in a fruit (containing Sorbon T-20 as a spreader/sticker at a final concentration of 200 µL/L) diluted with water to have concentrations of compounds shown in Table 7 were prepared. The mass of fruit of grape (variety: Red Globe) purchased on the market was measured. Then, the prepared agents for increasing a sugar content in a fruit were applied by spraying to the fruit of grape, which was then allowed to stand in an air-conditioned greenhouse (temperature: 25° C.). With the mass of the grape on the date of application being 100 g, the mass of the grape after the application was measured over time (date of application: May 16, 2011; dates of test: May 19, May 23, May 27, May 30, and Jun. 2, 2011). Next, on the assumption that the change in mass of the fruit was entirely due to the change in water content, the calculated value of the sugar content was determined from the amount of decrease in mass and the sugar content on the date (June 2) of the application (calculated as follows: "the sugar content (calculated value)=the sugar content (%) on the date of application×the mass (g) on the date of application/the mass (g) on the date of measurement"). In addition, as a control, the mass of untreated grape was measured in the same manner. The results are shown in Tables 7 and 8 and FIGS. 12 to 14.

Figure 12:
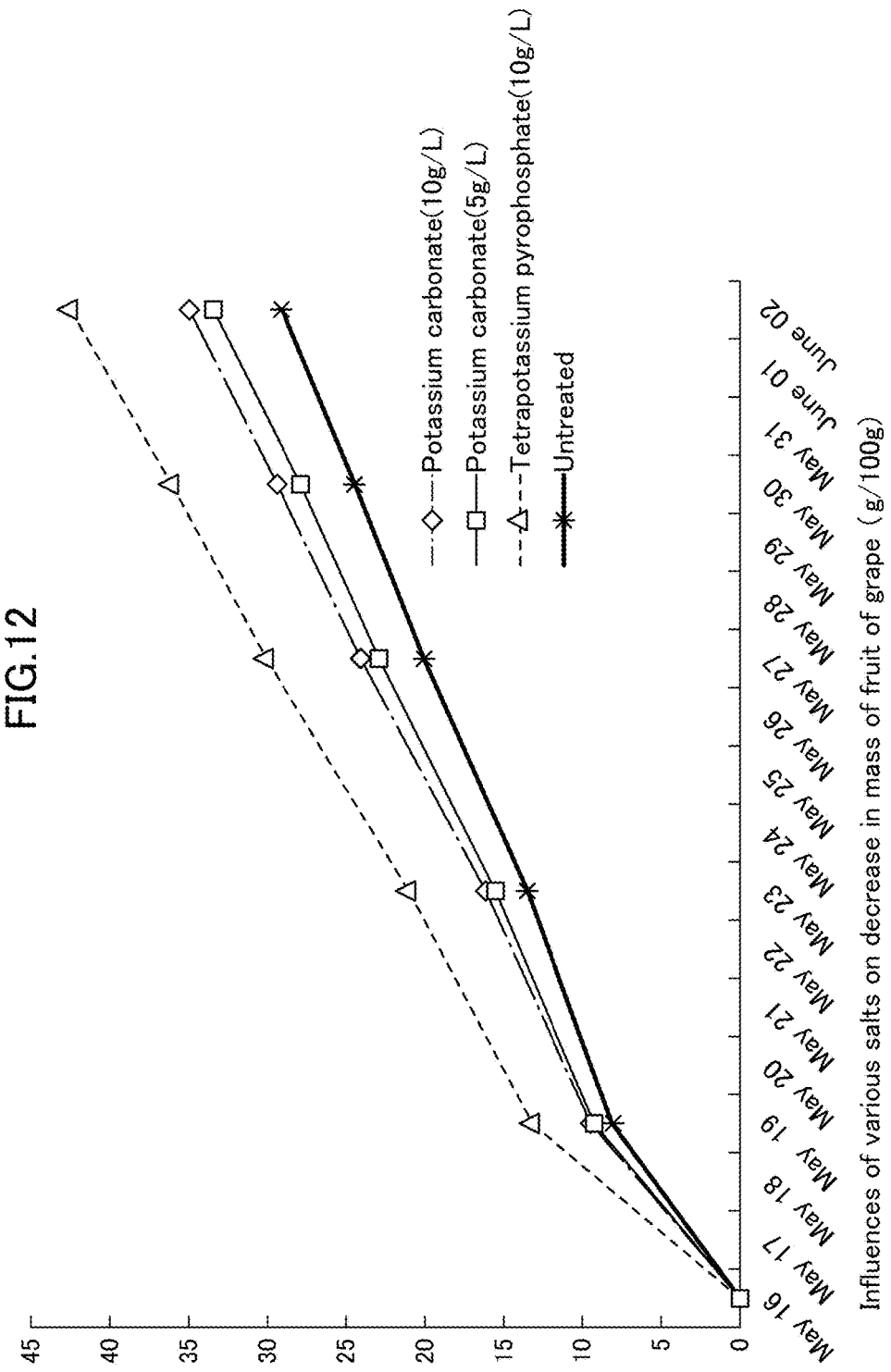
FIG. 12 is a graph showing the decrease ratio (%) of the mass of fruit on each date of measurement in Example 7.
Figure 13:
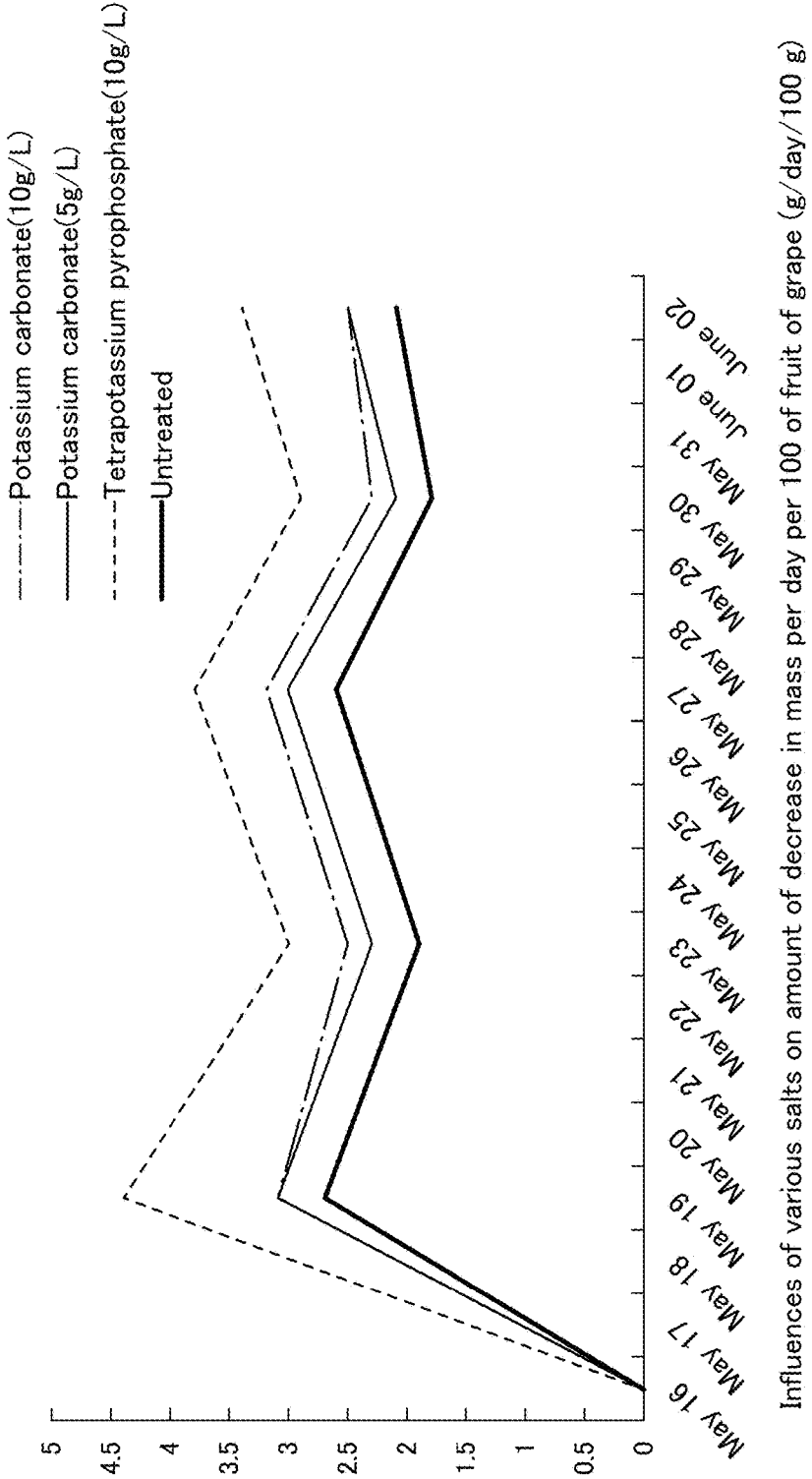
FIG. 13 is a graph showing the amount (g) of decrease in mass of fruit per day on each date of measurement per 100 g of the fruit in Example 7.
Figure 14:
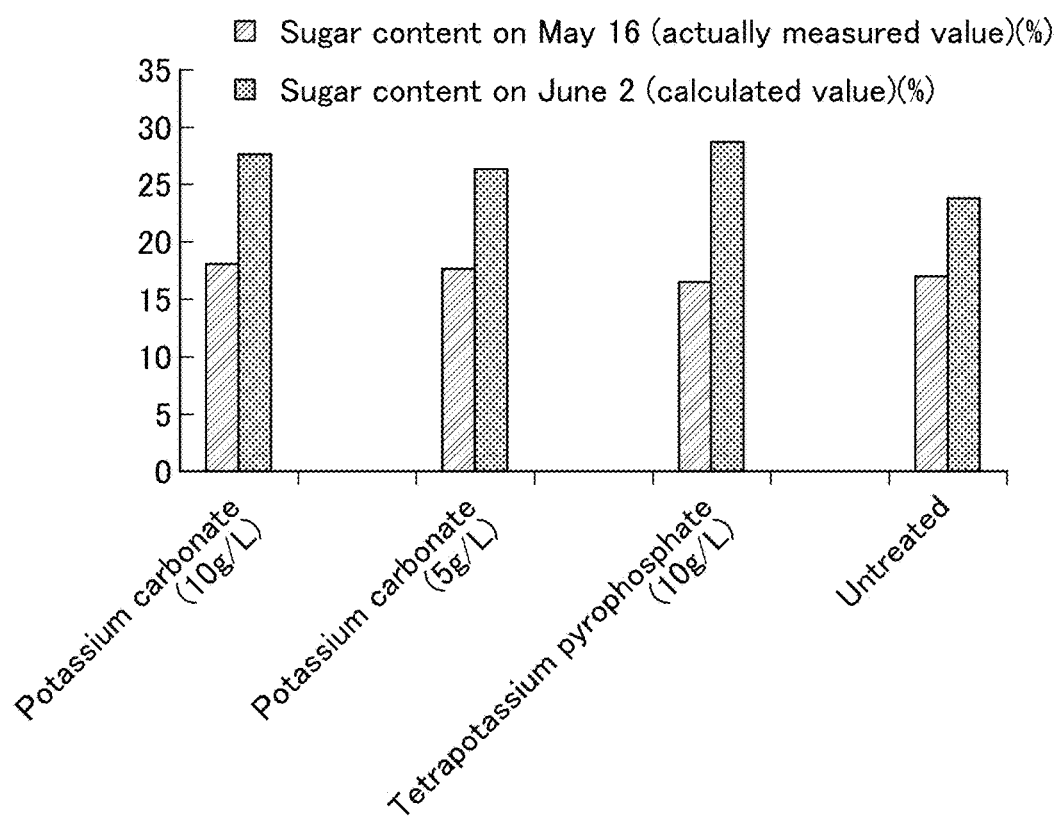
FIG. 14 is a graph in which the sugar content (%) (actually measured value) on the date of application and the sugar content (%) (calculated value) on the date of test are compared with each other in the case where each compound was applied in Example 7.

Note that the vertical axis in FIG. 12 represents the amount (g) of decrease in mass of the fruit of grape on each of the dates of measurement per 100 g of the fruit of grape on the date of application, the vertical axis in FIG. 13 represents the amount (g) of decrease per day of the fruit of grape on each of the dates of measurement per 100 g of the fruit of grape on the date of application, and the vertical axis in FIG. 14 represents the sugar content (%).

TABLE 7

|  | May 16 | May 19 | May 23 | May 27 | May 30 | Jun. 2 |
|---|---|---|---|---|---|---|
| Potassium carbonate (10 g/L) | 100 | 90.6 | 83.9 | 75.9 | 70.6 | 65 |
| Potassium carbonate (5 g/L) | 100 | 90.8 | 84.5 | 77 | 72.1 | 66.6 |
| Tetrapotassium pyrophosphate (10 g/L) | 100 | 86.7 | 78.9 | 69.8 | 63.8 | 57.3 |
| Untreated | 100 | 91.8 | 86.5 | 79.9 | 75.6 | 70.8 |

Each numeric value in the table represents the mass (g) of the fruit.

TABLE 8

|  | Sugar content (%) | |
|---|---|---|
|  | May 16 | Jun. 2 Calculated value |
| Potassium carbonate (10 g/L) | 18.2 | 28 |
| Potassium carbonate (5 g/L) | 17.6 | 26.5 |
| Tetrapotassium pyrophosphate (10 g/L) | 16.6 | 29 |
| Untreated | 17 | 24 |

The largest decrease in mass was that of the fruit of grape treated with the tetrapotassium pyrophosphate solution, and the mass of the fruit of grape 17 days later was 57.3% of the mass on the date of application. The mass was decreased to 65% by 10 g/L potassium carbonate, and 66.6% by 5 g/L potassium carbonate. On the other hand, the mass of the fruit of the untreated group after the same period had elapsed was 70.9% of the mass on the date of application. Accordingly, it can be seen that the decrease in mass of the fruit was promoted in each of the cases where these compounds were applied in comparison with the untreated case.

The highest ratio of decrease in mass per day was that of the potassium pyrophosphate. The ratio of decrease decreased in order of 10 g/L potassium carbonate and 5 g/L potassium carbonate. The lowest ratio of decrease was that of the untreated group.

The estimated sugar concentration (Brix %) in the fruit at the last time point was the highest in the fruit treated with potassium pyrophosphate, and was 29%, followed by 28% with 10 g/L potassium carbonate and by 26.5% with 5 g/L potassium carbonate in this order.

Example 8

An agent for increasing a sugar content in a fruit (containing Sorbon T-20 as a spreader/sticker at a final concentration of 200 μL/L) diluted with water to have a potassium hydrogen carbonate concentration of 10 g/L was prepared. The masses of fruits of apple and cherry tomato purchased on the market were measured. Then, the prepared agent for increasing a sugar content in a fruit was applied by spraying to the fruits. The fruits were allowed to stand still in an air-conditioned greenhouse, and the masses of the apples and cherry tomatoes were measured on the date of application (date of application: Nov. 30, 2011; date of test: Dec. 5, 2011). In addition, as a control, the masses of untreated apples and cherry tomatoes were measured in the same manner. Table 9 shows the results.

TABLE 9

| No. | Name of fruits | Treated/Untreated | Mass (g) before application | Mass (g) on date of test | Estimated amount (g) of transpiration | Estimated transpiration ratio (%) | Estimated transpiration ratio (average) (%) | Transpiration ratio |
|---|---|---|---|---|---|---|---|---|
| 1 | Apple | Untreated | 242.71 | 236.93 | 5.78 | 2.38 | 2.14 | 1.00 |
| 2 | Apple | Untreated | 262.01 | 256.31 | 5.70 | 1.95 | | |
| 3 | Apple | Treated | 286.31 | 274.65 | 11.66 | 3.72 | 3.54 | 1.65 |
| 4 | Apple | Treated | 272.84 | 263.69 | 9.15 | 3.35 | | |
| 5 | Cherry tomato | Untreated | 209.78 | 198.78 | 11.00 | 5.24 | | 1.00 |
| 6 | Cherry tomato | Treated | 215.05 | 193.30 | 21.75 | 10.12 | | 1.93 |

The estimated transpiration ratio (%) was calculated by "the estimated amount (g) of transpiration/the mass (g) before application×100."

The transpiration ratio was calculated by "the estimated transpiration ratio of the target sample (treated by application of potassium hydrogen carbonate or untreated)/the estimated transpiration ratio of the untreated sample."

In the period of the experiment, 2.14% of water was estimated to be lost on average from the untreated fruit of apple, whereas 3.54% of water was estimated to be lost from the treated fruit of apple. The water lost from the treated fruit was 1.65 times of that lost from the untreated fruit.

Likewise, in the case of the cherry tomato, the amount of transpiration from the untreated fruit was estimated to be 5.24%, whereas the amount lost from the treated fruit was estimated to be 10.12%. The amount of water lost from the treated fruit reached 1.93 times of water lost from the untreated fruit.

From the results described above, it can be said that the agent for increasing a sugar content in a fruit of the present invention is capable of increasing the amount of transpiration and, in turn, increasing the sugar content in the cases of not only grape, but also apple and tomato in the same manner.

Example 9

Solutions (containing Sorbon T-20 as a spreader/sticker at a final concentration of 200 μL/L) diluted with water to have concentrations of the compounds listed in Table 10 of 10 g/L were applied by spraying to grape clusters in the same manner, and the transpiration ratios were investigated 8 days later.

Table 10 shows the results.

TABLE 10

Estimated transpiration ratio (%) of clusters of grape (variety: Crimson) subjected to immersion treatment (8 days after treatment)

| No. | Name of compound | First | Second | Average |
|---|---|---|---|---|
| 1 | Potassium hydrogen carbonate | 33 | 28 | 31 |
| 2 | Sodium hydrogen carbonate | 33 | 28 | 30 |
| 3 | Potassium carbonate | 35 | 31 | 33 |
| 4 | Sodium carbonate | 32 | — | 32 |
| 5 | Magnesium carbonate | 32 | — | 32 |
| 6 | Potassium acetate | 35 | 35 | 35 |
| 7 | Sodium acetate trihydrate | 35 | 33 | 34 |
| 8 | Dipotassium hydrogen phosphate | 28 | — | 28 |
| 9 | Disodium hydrogen phosphate | 35 | 28 | 31 |
| 10 | Tetrapotassium pyrophosphate | 32 | — | 32 |
| 11 | Tripotassium citrate | 32 | 28 | 30 |

TABLE 10-continued

Estimated transpiration ratio (%) of clusters of grape (variety: Crimson) subjected to immersion treatment (8 days after treatment)

| No. | Name of compound | First | Second | Average |
|---|---|---|---|---|
| 12 | Disodium succinate | 31 | — | 31 |
| 13 | Untreated (control) | 21 | 28 | 25 |
| 14 | Ammonium carbonate | 25 | 28 | 26 |
| 15 | Ammonium hydrogen carbonate | 25 | 25 | 25 |
| 16 | Potassium chloride | 25 | — | 25 |
| 17 | Magnesium chloride | 25 | — | 25 |

TABLE 10-continued

Estimated transpiration ratio (%) of clusters of grape
(variety: Crimson) subjected to immersion treatment
(8 days after treatment)

| No. | Name of compound | First | Second | Average |
|---|---|---|---|---|
| 18 | Sodium chloride | 22 | — | 22 |
| 19 | Potassium sulfate | 24 | — | 24 |
| 20 | Magnesium sulfate | 23 | — | 23 |
| 21 | Ammonium sulfate | 21 | 23 | 22 |
| 22 | DL-Potassium tartrate | 22 | — | 22 |
| 23 | DL-Sodium lactate | 26 | 25 | 26 |

From Table 10, it can be seen that the compound represented by the formula MX, wherein M is alkali metal ion or alkaline earth metal ion, and X is hydrogen carbonate ion, carbonate ion, acetate ion, phosphate ion (including hydrogen phosphate ion and pyrophosphate ion), citrate ion, or succinate ion, can promotes the transpiration from fruit to decrease the mass, and thereby increase the sugar content in the fruit (Nos. 1 to 12).

On the other hand, it can be seen that when similar compounds in which M is ammonium ion, or X is chloride ion, sulfate ion, tartrate ion, or lactate ion are used, the transpiration action (mass-decreasing action) on the fruit is almost the same as in the untreated case, and hence these similar compounds are unable to increase the sugar content in the fruit (Nos. 13 to 23).

Example 10

Solutions (containing Sorbon T-20 as a spreader/sticker at a final concentration of 200 μL/L) diluted with water to have concentrations of the compounds listed in Table 11 of 10 g/L (100-times diluted samples) or 20 g/L (50-times diluted samples) were applied by spraying to tomato, grape, and Mikan in the same manner, and the ratios of decrease in weights of the fruits were investigated 6 days later.

Table 11 shows the results.

TABLE 11

Ratio (%) of decrease in body weight of fruit, to which agent
was applied, 6 days after treatment

| No. | Agent | Dilution ratio | Tomato | Mikan |
|---|---|---|---|---|
| 1 | Sodium acetate | 100 | 15.6 | 11.2 |
| 2 | Sodium acetate | 50 | 14.5 | 11.4 |
| 3 | Potassium carbonate | 100 | 18.0 | 12.4 |
| 4 | Potassium carbonate | 50 | 21.1 | 12.0 |
| 5 | Potassium hydrogen carbonate | 100 | 14.8 | 12.6 |
| 6 | Sodium carbonate | 100 | 12.7 | 10.4 |
| 7 | Sodium hydrogen carbonate | 100 | 12.8 | 11.4 |
| 8 | Potassium pyrophosphate | 100 | 13.8 | 10.4 |
| 9 | Untreated (water) | 100 | 9.4 | 9.6 |

From Table 11, it can be seen that each of the solutions of the compounds decreased the weights of tomato and Mikan.

Example 11

Effect of Agent for Increasing Sugar Content in Fruit on Acceptability of Fruit

The degree of acceptability of Pinot noir was compared between Example 1 and Example 2 after the date of the last measurement of the sugar content.

As in the case where agriculture workers check whether or not a berry can be used for wine, the criteria of the acceptability were based the appearance (appearance associated with mold, rot, or the like, whether or not the fruit juice or fruit pulp was lost, and the like), taste (whether or not the berry was normal, when eaten, and the like), and odor (whether or not a foreign odor or the like was present). A berry having no problem in terms of any of the appearance, taste, and odor was determined to be acceptable, and a berry having any problem was determined to be not acceptable. Table 12 shows the results. Note that the acceptable ratio of the untreated group is an average acceptable ratio of Examples 1 and 2.

TABLE 12

| Sample | | Acceptable ratio (%) of fruit |
|---|---|---|
| Example 1 | Potassium hydrogen carbonate (10 g/L) | 80 |
| Example 1 | Potassium hydrogen carbonate (5 g/L) | 75 |
| Example 2 | Potassium hydrogen carbonate preparation (10 g/L) | 95 |
| Example 2 | Sodium hydrogen carbonate preparation (10 g/L) | 95 |
| Untreated | | 10 |

The results of the acceptability test showed that most of the untreated fruits (berries) were rotten or dry, and unsuitable for winemaking.

In contrast, the ratio of the fruits unsuitable for winemaking decreased in the cases of the treatment with potassium hydrogen carbonate (samples of Example 1). Meanwhile, the ratio of fruits unsuitable for wine remarkably decreased in the case where the potassium hydrogen carbonate preparation or sodium hydrogen carbonate preparation to which the vegetable oils were added was applied (samples of Example 2). It is conceivable that such an effect of increasing the acceptable ratio is an effect accompanying the increase in sugar content.

Example 12

Influence on Recovery from Calcium Deficiency (Method)

In general, calcium deficiency in lettuce and celery occurs from summer to fall. Heart rot symptom develops in lettuce, and change in color and blackening of new leaves develop in celery. In addition, tipburn may also occur in lettuce. A 10 g/L aqueous potassium hydrogen carbonate solution was applied at intervals of one week to lettuce and celery in which no symptom of calcium deficiency had yet developed, and whether or not the symptom became milder than that of an untreated group was observed. Five plants were subjected to each treatment, and the degree of the symptom of calcium deficiency was determined on the basis of the degree of browning of leaves at the harvest. Table 13 shows the results.

(Degree of Calcium Deficiency)

0: no browning, 0.5: browning occurred only in very small portions on the edges of leaves, 1.0: browning occurred in portions on the edges of spikes, 2.0: browning occurred from edges of leaves to the inside, 3.0: the degree of browning was considerable, 5.0: the browning of leaves was remarkable.

Degree of occurrence=(Index 5×the number of plants in which the corresponding blowing occurred+ Index 3×the number of plants in which the corresponding blowing occurred+Index 2×the number of plants in which the corresponding blowing occurred+Index 1×the number of plants in which the corresponding blowing occurred+ Index 0.5×the number of plants in which the corresponding blowing occurred)/5 plants

TABLE 13

| | Degree of occurrence of calcium deficiency | |
|---|---|---|
| | Groups treated with aqueous potassium hydrogen carbonate solution | Untreated groups |
| Lettuce (Great Lakes) | 0.2 | 1.2 |
| Celery | 0.3 | 1.5 |

As shown in Table 13, no browning of leaves occurred and almost no calcium deficiency symptom was observed in the plants treated with potassium hydrogen carbonate, in contrast to the untreated plants.

Example 13

Influence on Water-Soaked Symptom

The water-soaked symptom in cherry is known to be caused by calcium deficiency. In this respect, an investigation was made as to whether or not the degree of occurrence of water-soaked symptom 28 days after the date of the first application was different between untreated cherries and cherries to which an aqueous potassium hydrogen carbonate solution (5 g/L) was applied three times at intervals of 7 days one month before the harvest time. Table 14 shows the results.

The occurrence (%) of water-soaked symptom=the number of cherries in which the water-soaked symptom occurred/the number of cherries tested×100

TABLE 14

| | Occurrence (%) of water-soaked symptom | |
|---|---|---|
| | Group to which aqueous potassium hydrogen carbonate solution was applied | Untreated group |
| Cherry (Sato Nishiki) | 7 | 24 |

As can be understood from Table 14, the application of the aqueous potassium hydrogen carbonate solution suppressed the occurrence of the water-soaked symptom.

The water-soaked symptom was less frequent in the group to which the aqueous potassium hydrogen carbonate solution was applied presumably because the transpiration was activated, and the absorption of water through the roots increased by that much. In general, calcium deficiency is hardly recovered by application on the surfaces of leaves. However, recovery from calcium deficiency is easily achieved by increasing the absorption through roots.

The water-soaked symptom was less frequent in the cherries to which the aqueous potassium hydrogen carbonate solution was applied, presumably for the following reason. Specifically, the treatment activated the transpiration, and the amount of absorption increased with this activation. As a result, the amount of calcium absorbed through roots with water increased. Hence, the occurrence of the water-soaked symptom (calcium deficiency) was suppressed.

Example 14

Influence on Prevention of Fruit Cracking of Fruit

To each of the plants shown in Table 15 below, an aqueous potassium hydrogen carbonate solution (10 g/L) was applied three times at intervals of one week about one month before the harvest time. Each of the plants was harvested four weeks later. The degree of the fruit cracking of the fruit was compared with that of untreated fruit, and a fruit cracking-suppression ratio was determined. Table 15 shows the results.

The fruit cracking ratio (%)=the number of pieces of the fruit which underwent fruit cracking/the total number of pieces of the fruit×100

The fruit cracking-suppression ratio (%)=(1−the fruit cracking ratio (%) of a treated group/the fruit cracking ratio (%) of an untreated group)×100

TABLE 15

| | Fruit cracking-suppression ratio |
|---|---|
| Cherry (Sato Nishiki) | 98 |
| Grape (Nagano Purple) | 97 |
| Tomato (Regina) | 95 |
| Grape (Riesling) | 98 |

As can be understood from Table 15, the fruit cracking of the fruit was remarkably suppressed in each of the plants treated with potassium hydrogen carbonate.

Example 15

Influence (1) on Amino Acid Content

To each of the plants shown in Table 16 below, an aqueous potassium hydrogen carbonate solution (5 g/L for lettuce and 10 g/L for the other plants) was applied three times at intervals of one week from one month before the harvest. The plants were harvested three weeks after the start of the application. Untreated plants not treated with the aqueous potassium hydrogen carbonate solution were harvested at the same time. After the harvest, the total amount of amino acids in each sample was determined, and the ratio of the total amount of amino acids in the plant treated with potassium hydrogen carbonate to the total amount of amino acids in the untreated plant was determined. Table 16 shows the results.

TABLE 16

| | Amino acid concentration ratio (treated/untreated) |
|---|---|
| Grape (fruit: Cabernet Sauvignon) | 2.2 |
| Tomato (fruit: Regina) | 1.8 |
| Lettuce (leaves: Great Lakes) | 1.5 |

TABLE 16-continued

|  | Amino acid concentration ratio (treated/untreated) |
|---|---|
| Wheat (grains: Norin No. 61) | 1.2 |
| Rice plant (grains: Nipponbare) | 1.2 |

As shown in Table 16, the amino acid concentration of each of the plants treated with potassium hydrogen carbonate increased by 1.2 to 2.2 times in comparison with the corresponding untreated plant.

Example 16

Influence (2) on Amino Acid Content

To the fruit of grape in a farm field before harvest, potassium hydrogen carbonate diluted with water to a concentration of 10 g/L (Table 17) or 20 g/L (Table 18) was applied three times in total at intervals of 7 days. The grape was harvested 21 days after the first application, and the masses of amino acids contained in each of the fruit of grape treated with potassium hydrogen carbonate and untreated fruit of grape were measured. In addition, the degree of increase in the concentration of each amino acid in the grape treated with potassium hydrogen carbonate in comparison with the concentration of the amino acid in the untreated grape was determined as a ratio of "the concentration of the amino acid in the grape treated with potassium hydrogen carbonate/the concentration of the amino acid in the untreated grape." Moreover, the sugar contents in the grape treated with potassium hydrogen carbonate and the untreated grape were also measured, and the ratio (the sugar content in the grape treated with potassium hydrogen carbonate/the sugar content in the untreated grape) was determined. Tables 17 and 18 show the results.

Note that the abbreviations in Tables 17 and 18 have the following meanings:

Arg: arginine, $GluNH_2$: glutamine, Orn: ornithine, Ala: alanine, $NH_3$: ammonia, Cit: citrulline, $AspNH_2$: asparagine, a-ABA: α-amino-n-butyric acid, Glu: glutamic acid, Asp: aspartic acid, Thr: threonine, Ser: serine, Lys: lysine, His: histidine, Gly: glycine, Phe: phenylalanine, Sar: sarcosine, Val: valine, Cys: cysteine, b-AiBA: β-aminoisobutyric acid, PEA: phosphoethanolamine, a-AAA: α-aminoadipic acid, $EOHNH_2$: ethanolamine, b-Ala: β-alanine, Leu: leucine, g-ABA: γ-aminoacetic acid, Ile: isoleucine, Met: methionine, Urea: urea, Trp: tryptophan, Tyr: tyrosine, and Cysthi: cystathionine.

TABLE 17

| | Aqueous potassium hydrogen carbonate solution (10 g/L) | | |
|---|---|---|---|
| Name of component | Treated Mass (ng) | Untreated Mass (ng) | Ratio |
| Arg | 1383.991 | 129.9532 | 10.658 |
| $GluNH_2$ | 347.152 | 49.269 | 7.046 |
| Orn | 23.882 | 3.569 | 6.692 |
| Ala | 601.952 | 115.117 | 5.229 |
| $NH_3$ | 438.689 | 93.075 | 4.713 |
| Cit | 11.464 | 2.453 | 4.673 |
| $AspNH_2$ | 14.746 | 3.699 | 3.987 |
| a-ABA | 9.038 | 2.784 | 3.246 |
| Glu | 1091.265 | 374.811 | 2.915 |
| Asp | 89.293 | 33.142 | 2.694 |

TABLE 17-continued

| | Aqueous potassium hydrogen carbonate solution (10 g/L) | | |
|---|---|---|---|
| Name of component | Treated Mass (ng) | Untreated Mass (ng) | Ratio |
| Thr | 342.259 | 130.891 | 2.615 |
| Ser | 360.511 | 139.468 | 2.585 |
| Lys | 18.865 | 10.673 | 1.768 |
| His | 96.252 | 59.597 | 1.615 |
| Gly | 25.939 | 18.700 | 1.553 |
| Phe | 51.201 | 33.536 | 1.527 |
| Sar | 62.178 | 48.916 | 1.271 |
| Val | 191.700 | 152.581 | 1.256 |
| Cys | 117.021 | 101.407 | 1.154 |
| b-AiBA | 9.663 | 8.557 | 1.129 |
| PEA | 87.942 | 85.224 | 1.032 |
| a-AAA | 3.261 | 3.063 | 1.031 |
| $EOHNH_2$ | 53.297 | 52.241 | 1.02 |
| b-Ala | 197.064 | 193.347 | 1.019 |
| Leu | 110.503 | 109.158 | 1.012 |
| g-ABA | 637.915 | 715.926 | 0.891 |
| Ile | 72.435 | 82.787 | 0.875 |
| Met | 6.131 | 7.311 | 0.839 |
| Urea | 105.062 | 144.541 | 0.757 |
| Trp | 4.840 | 7.552 | 0.641 |
| Tyr | 17.739 | 30.079 | 0.59 |
| Cysthi | 1.016 | 2.223 | 0.457 |
| Total | 1082.09 | 491.111 | 2.203 |
| Sugar content | 22.6% | 20.9% | 1.06 |

TABLE 18

| | Aqueous potassium hydrogen carbonate solution (20 g/L) | | |
|---|---|---|---|
| Name of component | Treated Mass (ng) | Untreated Mass (ng) | Ratio |
| Arg | 2018.4554 | 129.9532 | 15.532 |
| Cit | 30.134 | 2.453 | 12.285 |
| Orn | 41.643 | 3.569 | 11.668 |
| $GluNH_2$ | 561.408 | 49.269 | 11.395 |
| $AspNH_2$ | 26.684 | 3.699 | 7.214 |
| Ala | 709.236 | 115.117 | 6.161 |
| $NH_3$ | 450.976 | 93.075 | 4.845 |
| a-ABA | 9.898 | 2.784 | 3.555 |
| Ser | 495.547 | 139.468 | 3.553 |
| Thr | 415.421 | 130.891 | 3.174 |
| Asp | 86.648 | 33.142 | 2.614 |
| Lys | 26.170 | 10.673 | 2.452 |
| His | 137.818 | 59.597 | 2.312 |
| Phe | 65.750 | 33.536 | 1.961 |
| Glu | 693.282 | 374.811 | 1.85 |
| Gly | 34.546 | 18.700 | 1.847 |
| g-ABA | 1298.441 | 715.926 | 1.811 |
| PEA | 140.112 | 85.224 | 1.644 |
| Val | 242.163 | 152.581 | 1.587 |
| Sar | 74.309 | 48.916 | 1.5191 |
| Cys | 142.979 | 101.407 | 1.41 |
| a-AAA | 4.352 | 3.063 | 1.408 |
| Leu | 151.405 | 109.158 | 1.387 |
| Met | 9.698 | 7.311 | 1.325 |
| b-Ala | 232.373 | 193.347 | 1.202 |
| 1Mehis | 1.184 | 1.015 | 1.167 |
| $EOHNH_2$ | 76.497 | 52.241 | 1.164 |
| Ile | 95.120 | 82.787 | 1.149 |
| b-AiBA | 9.588 | 8.557 | 1.12 |
| Tyr | 29.898 | 30.079 | 0.994 |
| Trp | 7.348 | 7.552 | 0.973 |
| Cysthi | 0.667 | 2.223 | 0.3 |
| Total | 1239.923 | 491.126 | 2.525 |
| Sugar content | 25.9% | 20.9% | 1.24 |

As can be understood from the results in Tables 17 and 18, the amounts of most of the amino acids increased in the grape treated with potassium hydrogen carbonate in comparison with the untreated case. However, the increase ratio of the amount of an amino acid in the grape treated with potassium hydrogen carbonate to the amount of the amino acid in the untreated grape varies among the amino acids, and this cannot be explained by the concentration of each amino acid due to loss of water in the fruit by transpiration alone. It is conceivable that the addition of potassium hydrogen carbonate caused some mechanism to act, so that the amounts of amino acids themselves increased.

Example 17

Production of High Quality Dried Grape

To fruit of trellised grape (variety: Pinot noir), an aqueous potassium hydrogen carbonate solution (20 g/L) was applied three times at intervals of one week. The fruit was harvested 21 days after the first application, and the sugar content, acidity, and amino acid concentration were measured. In addition, the harvested fruit was kept in an air-conditioned greenhouse (25° C.) for 10 days, and the drying state of the fruit was observed. Table 19 shows the results.

TABLE 19

Comparison of states of the fruits at harvest time

| | Sugar content (%) | Acidity | Amino acid concentration (μg/L) | State 10 days after harvest |
|---|---|---|---|---|
| Treated with aqueous potassium hydrogen carbonate solution | 46 | 0.8 | 2800 | became almost completely dried, and took a dried grape state. |
| Untreated | 21 | 0.4 | 580 | retained sufficient water yet. |

As can be understood from Table 19, the grape treated with potassium hydrogen carbonate dried faster than the untreated grape. This made it possible to produce dried grape in a shorter time. In this experiment, potassium hydrogen carbonate was applied to the grape before the harvest. However, since the compound of the present invention can promote the transpiration, even when applied to harvested fruit, it is conceivable that, also when potassium hydrogen carbonate is applied to harvested grape, the grape can be dried in a short period in the same manner.

Example 18

Production of High Quality Wine

<Production of High Quality Wine Using High Quality Grape to which Aqueous Potassium Hydrogen Carbonate Solution was Applied>

Fruit of grape (Chardonnay) to which an aqueous potassium hydrogen carbonate solution (10 g/L) was applied three times at intervals of 7 days from three weeks before the expected harvest date was harvested 21 days after the first application, and wine was produced therefrom in an ordinary manner. The flavor, taste, color, and the like of the produced wine were tested. All the flavor, taste, and color were superior to those of conventional wine. In addition, no adverse effect was observed on the fermentation.

INDUSTRIAL APPLICABILITY

The present invention makes it possible to increase a sugar content in a fruit by a simple method, without being restricted by a cultivation area of a plant or a climatic environment. Hence, the present invention is very industrially useful.

The invention claimed is:

1. A method for increasing a sugar content in a fruit of a plant, comprising applying to the plant a composition comprising:
    a) a compound represented by the formula MX as an active ingredient; and
    b) a surfactant comprising polyoxyethylene cocoamine, polyoxyethylene alkyl ether, polyoxyethylene sorbitan monolaurate, and diglycerin monooleate, and
wherein M represents potassium ion, and X represents carbonate ion or hydrogen carbonate ion, and wherein the plant is grape.

2. The method according to claim 1, wherein the composition is applied in a period from 2 months before an expected harvest date or a harvest date of the fruit to 2 months after the expected harvest date or the harvest date.

3. The method according to claim 1, wherein the compound represented by the formula MX is applied to the plant at a concentration in a range from 1 g/L to 100 g/L.

4. The method according to claim 1, wherein the compound represented by the formula MX is applied to the plant at a dose in a range from 1 kg/ha to 30 kg/ha.

5. The method according to claim 1, wherein the composition is applied only to a fruit portion of the plant.

6. The method according to claim 1, wherein the composition is applied to a fruit of the plant after harvest.

7. A method for producing a fruit wine, comprising using as a raw material a fruit and applying to the fruit a composition comprising:
    (a) a compound represented by the formula MX as an active ingredient; and
    (b) a surfactant comprising polyoxyethylene cocoamine, polyoxyethylene alkyl ether, polyoxyethylene sorbitan monolaurate, and diglycerin monooleate, and
    wherein M represents potassium ion, and X represents carbonate ion or hydrogen carbonate ion, and wherein the fruit is grape.

8. A method for producing dried grape, comprising adding to the grape a composition comprising:
    (a) a compound represented by the formula MX as an active ingredient; and
    (b) a surfactant comprising polyoxyethylene cocoamine, polyoxyethylene alkyl ether, polyoxyethylene sorbitan monolaurate, and diglycerin monooleate, and
    wherein M represents potassium ion, and X represents carbonate ion or hydrogen carbonate ion.

* * * * *